(12) United States Patent
Rivolta et al.

(10) Patent No.: US 12,209,254 B2
(45) Date of Patent: *Jan. 28, 2025

(54) HUMAN OTIC PROGENITOR IDENTIFICATION AND ISOLATION

(71) Applicant: THE UNIVERSITY OF SHEFFIELD, Sheffield (GB)

(72) Inventors: Carlos Marcelo Nicolas Rivolta, Sheffield (GB); Sarah Louise Boddy, Sheffield (GB)

(73) Assignee: THE UNIVERSITY OF SHEFFIELD, Sheffield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/182,829

(22) Filed: Mar. 13, 2023

(65) Prior Publication Data

US 2023/0313134 A1   Oct. 5, 2023

Related U.S. Application Data

(63) Continuation of application No. 16/329,935, filed as application No. PCT/GB2017/052707 on Sep. 14, 2017, now Pat. No. 11,634,687.

(30) Foreign Application Priority Data

Sep. 15, 2016  (GB) ..................................... 1615714

(51) Int. Cl.
| | |
|---|---|
| *C07K 16/28* | (2006.01) |
| *C07K 16/18* | (2006.01) |
| *C07K 16/30* | (2006.01) |
| *C12N 5/0797* | (2010.01) |
| *G01N 33/48* | (2006.01) |
| *G01N 33/50* | (2006.01) |
| *G01N 33/53* | (2006.01) |
| *G01N 33/569* | (2006.01) |

(52) U.S. Cl.
CPC ............ *C12N 5/0623* (2013.01); *C07K 16/18* (2013.01); *C07K 16/28* (2013.01); *C07K 16/2896* (2013.01); *C07K 16/3084* (2013.01); *G01N 33/48* (2013.01); *G01N 33/53* (2013.01); *G01N 33/56966* (2013.01); *G01N 2333/705* (2013.01); *G01N 2333/70596* (2013.01); *G01N 2333/71* (2013.01); *G01N 2333/7452* (2013.01); *G01N 2333/916* (2013.01)

(58) Field of Classification Search
CPC .... G01N 33/48; G01N 33/5005; G01N 33/53; G01N 2333/705; G01N 2333/70596; G01N 2333/71; C07K 16/28; C07K 16/2896; C07K 16/3084; C07K 14/705; C07K 14/70596; C07K 14/71; C12N 5/0623; C12N 5/0607; C12N 5/0696; C12N 5/0647; C12N 5/0621
See application file for complete search history.

(56) References Cited

U.S. PATENT DOCUMENTS

| | | | |
|---|---|---|---|
| 6,436,704 B1 | 8/2002 | Roberts et al. | |
| 6,534,052 B1 | 3/2003 | Xiao et al. | |
| 8,241,897 B2 | 8/2012 | Klassen et al. | |
| 11,634,687 B2 * | 4/2023 | Rivolta | G01N 33/48 |
| | | | 435/377 |
| 2003/0157078 A1 | 8/2003 | Hall et al. | |
| 2005/0287127 A1 | 12/2005 | Li et al. | |
| 2007/0250942 A1 | 10/2007 | Enikolopov et al. | |
| 2014/0004556 A1 | 1/2014 | Heller et al. | |
| 2015/0017133 A1 | 1/2015 | Young et al. | |

FOREIGN PATENT DOCUMENTS

| | | |
|---|---|---|
| CN | 101668848 | 3/2010 |
| JP | 2015522257 | 8/2015 |
| RU | 2525223 | 8/2014 |
| WO | 02086082 | 10/2002 |
| WO | 2009007746 | 1/2009 |
| WO | 2012103012 | 8/2012 |
| WO | 2013123292 | 8/2013 |

OTHER PUBLICATIONS

Magarinos et al. Early development of the vertebrate inner ear. Anat Record 295: 1775-1790, 2012.*
Canadian Application No. 3034529, "Office Action," mailed Nov. 1, 2023, 7 pages.
Brazilian Application No. 112019004749-2, Office Action mailed on Feb. 26, 2024, 4 pages.
"FlowCellect™ Human iPS Cell Characterization Kit (100 Tests)", Catalog No. FCSC100107, Dec. 2012, 15 pages.
U.S. Appl. No. 16/329,935, "Non-Final Office Action", Jun. 2, 2022, 13 pages.
U.S. Appl. No. 16/329,935, "Notice of Allowance", Dec. 14, 2022, 10 pages.
Andrews et al., "Comparative analysis of cell surface antigens expressed by cell lines derived from human germ cell tumours", International Journal of Cancer, vol. 66, 1996, pp. 806-816.

(Continued)

*Primary Examiner* — Bridget E Bunner
(74) *Attorney, Agent, or Firm* — Kilpatrick Townsend & Stockton LLP

(57) ABSTRACT

The present invention relates generally to the identification and isolation of human otic progenitor cells. More specifically, the present invention relates to a method of using cell markers to identify and isolate human otic progenitor cells from a mixed population of cells, methods of enrichment and production of human otic progenitor cells, and associated kits for use in identification and/or isolation of human otic progenitor cells, wherein the cell markers are selected from SSEA1 (CD15), disialoganglioside GD3, TRA-2-49 (liver/bone/kidney alkaline phosphatase), SSEA4, ganglioside GD2 and CD141.

17 Claims, 11 Drawing Sheets

(56) References Cited

OTHER PUBLICATIONS

Andrews et al., "Different Patterns of Glycolipid Antigens are Expressed following Differentiation of TERA-2 human embryonal carcinoma cells induced by retinoic acid, hexamethylene bisacetamide (HMBA) or bromodeoxyuridine (BUdR)", Differentiation, vol. 43, Feb. 13, 1990, pp. 131-138.
Australian Application No. 2017328903, "Examination Report", Nov. 18, 2022, 4 pages.
Boddy et al., "Generation of Otic Lineages from Human Induced Pluripotent Stem Cells", Human Gene Therapy, vol. 24, No. 5, May 1, 2013, pp. A26-A27.
Boddy et al., "Inner Ear Progenitor Cells can be Generated in Vitro from Human Bone Marrow Mesenchymal Stem Cells", Regenerative Medicine, vol. 7, No. 6, Nov. 1, 2012, pp. 757-767.
Boddy et al., "Purification of hESC-Derived Otic Progenitors from Heterogeneous Cell Populations", Annual Conference of the British Society for Gene and Cell Therapy, vol. 28, No. 8, Aug. 1, 2017, p. A27.
Chen et al., "Restoration of Auditory Evoked Responses by Human ES-Cell-Derived Otic Progenitors", Nature, vol. 490, No. 7419, Sep. 12, 2012, 7 pages.
Chile Application No. 201900682, "Search Report and Written Opinion", Jul. 22, 2020, 24 pages.
Chinese Application No. 201780056911.8, "Office Action", May 7, 2022, 10 pages.
Chinese Application No. 201780056911.8, "Office Action", Dec. 14, 2021, 15 pages.
Chinese Application No. 201780056911.8, "Office Action", Aug. 31, 2022, 8 pages.
Colombian Application No. NC2019/0002095, "Office Action", May 11, 2021, 12 pages.
Dominici et al., "Minimal Criteria for Defining Multipotent Mesenchymal Stromal Cells. The International Society for Cellular Therapy Position Statement", Cytotherapy, vol. 8, No. 4, 2006, pp. 315-317.
Draper et al., "Surface Antigen Markers", Handbook of Stem Cells, 31.1, Academic Press, 2012, pp. 375-381.
Draper et al., "Surface Antigens of Human Embryonic Stem Cells: Changes Upon Differentiation in Culture", Journal of Anatomy, vol. 200, No. 3, Mar. 2002, pp. 249-258.
Durbas et al., "GD2 ganglioside specific antibody treatment downregulates PI3K/Akt/mTOR signaling network in human neuroblastoma cell lines", International journal of oncology, vol. 47 No. 3, 2015, pp. 1143-1159.
GB1615714.1, "Combined Search and Examination Report", Apr. 26, 2017, 9 pages.
Hozawa et al., "Hearing and Glycoconjugates: Localization of Le-y, Le-x and Sialosyl-Le-x in Guinea Pig Cochlea, Particularly at the Tectorial Membrane and Sensory Epithelia of the Organ of Corti", Glycobiology, vol. 3, No. 1, Feb. 1993, pp. 47-55.
Indonesian Application No. P00201902238, "Office Action", Sep. 4, 2021, 4 pages.
Israeli Application No. 265288, "Office Action", Sep. 12, 2022, 3 pages.
Indian Application No. 201917009516, "First Examination Report", Jul. 29, 2021, 6 pages.
Japanese Application No. 2019-511989, "Office Action", Jan. 20, 2022, 4 pages.
Japanese Application No. 2019-511989, "Office Action", Aug. 3, 2021, 6 pages.
Kannagi et al., "Stage-Specific Embryonic Antigens (SSEA-3 and -4) are Epitopes of a Unique Globo-series Ganglioside Isolated from human teratocarcinoma Cells", The European Molecular Biology Organization, vol. 2 No. 12, 1983, pp. 2355-2361.
Kerr et al., "Expression of Pluripotent Stem Cell Markers in the Human Fetal Testis", Stem Cells, vol. 26, No. 2, Feb. 2008, pp. 412-421.
Koehler et al., "Generation of Inner Ear Organoids Containing functional hair cells from human pluripotent stem cells", Nature biotechnology, vol. 35 No. 6, Jun. 2017, pp. 583-591.
Korean Application No. 10-2019-7007122, "Office Action", Oct. 27, 2021, 8 pages.
Meyer Zum Gottesberge et al., "Localization of the CD15-Epitope in the Inner Ear of the Developing Mouse", Cell and Tissue Research, vol. 283, No. 3, Feb. 1996, pp. 395-401.
Mutin et al., "Immunologic Phenotype of Cultured Endothelial Cells: Quantitative analysis of cell surface molecules", Tissue antigens, vol. 50 No. 5, Nov. 1997, pp. 449-458.
International Application No. PCT/GB2017/052707, "International Preliminary Report on Patentability", Mar. 28, 2019, 9 pages.
International Application No. PCT/GB2017/052707, "International Search Report and Written Opinion", Nov. 7, 2017, 13 pages.
Ronaghi et al., "Inner Ear Hair Cell-Like Cells from Human Embryonic Stem Cells", Stem Cells and Development, vol. 23, No. 11, Jun. 1, 2014, pp. 1275-1284.
Rosner et al., "Gangliosides and Neuronal Differentiation", Neurochemistry International, vol. 20, No. 3, Apr. 1992, pp. 339-351.
Russian Application No. 2019110990, "Office Action", Apr. 26, 2021, 6 pages.
Russian Application No. 2019110990, "Office Action", Aug. 25, 2021, 9 pages.
Russian Application No. 2019110990, "Office Action", Dec. 9, 2020, 8 pages.
Russian Application No. 2019110990, "Search Report", Dec. 7, 2020, 4 pages.
Singapore Application No. 11201901410S, "Written Opinion", May 27, 2020, 6 pages.
Singapore Application No. 11201901410S, "Written Opinion mailed Feb. 18, 2022".
Solter et al., "Monoclonal antibody defining a stage-specific mouse embryonic antigen (SSEA-1)", Proceedings of the National Academy of Sciences, vol. 75 No. 11, 1978, pp. 5565-5569.
Strakova et al., "Multipotent Properties of Myofibroblast Cells Derived from Human Placenta", Cell and Tissue Research, vol. 332, No. 3, 2008, 17 pages.
Stuhlmiller et al., "Serological response of non-human primates to human melanoma disialoganglioside GD3", Cancer Immunology, Immunotherapy, vol. 29 No. 3, 1989, pp. 205-210.
Tang et al., "Genetic Correction of Induced Pluripotent Stem Cells From a Deaf Patient With MYO7A Mutation Results in Morphologic and Functional Recovery of the Derived Hair Cell-like Cells", Stem Cells Translational Medicine, Mar. 24, 2016, pp. 561-571.
Xu et al., "Neural Ganglioside GD2 Identifies a Subpopulation of Mesenchymal Stem Cells in Umbilical Cord", Cellular Physiology and Biochemistry, vol. 23, 2009, pp. 415-424.

* cited by examiner

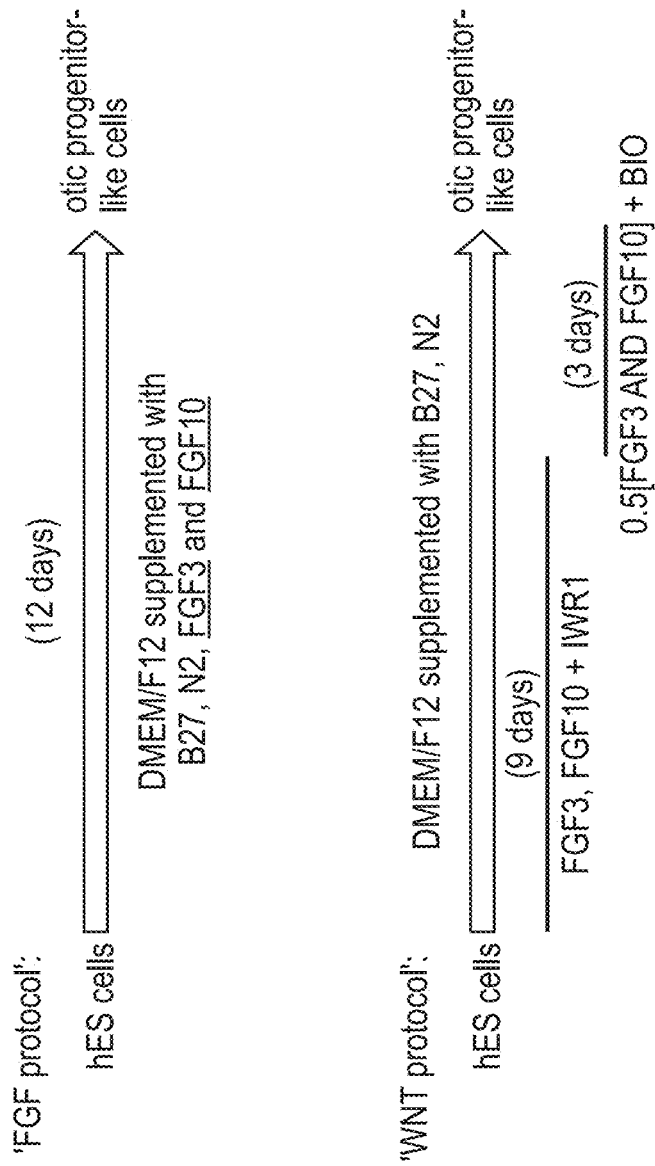

| Well | % positive | | | | | |
|------|---|---|---|---|---|---|
|      | 1 | 2 (Too low) | 3 | 4 (Too low) | 5 | |
| F-5  | 3.2 | 3.7 | 0.1 | 2.0 | 4.0 | |
| F-6  | 2.7 | 2.3 | 1.3 | 6.9 | 5.0 | |
| F-7  | 2.0 | 5.4 | 1.1 | 18.6 | 12.4 | |
| F-8  | 15.8 | 48.8 | 2.3 | 38.0 | 10.2 | |
| F-9  | 78.3 | 96.9 | 4.2 | 21.6 | 26.4 | |
| F-10 | 12.9 | 98.8 | 31.9 | 14.1 | 7.2 | |
| F-11 | 99.4 | 99.9 | 80.0 | 88.9 | 96.5 | |
| F-12 | 69.6 | 88.0 | 31.6 | 46.8 | 47.0 | |
| G-1  | 99.9 | 99.8 | 90.5 | 89.2 | 80.9 | |
| G-2  | 5.0 | 14.9 | 0.5 | 16.0 | 49.6 | |
| G-3  | 2.2 | 21.3 | 0.6 | 3.1 | 17.4 | |
| G-4  | 3.4 | 4.1 | 0.5 | 4.5 | 3.9 | |
| G-5  | 1.4 | 8.4 | 1.4 | 1.9 | 2.1 | |
| G-6  | 87.7 | 98.7 | 63.4 | 30.7 | 68.1 | |

Columns 1–3: H14s9/WNT protocol; Columns 4–5: Shef3.2/FGF protocol

FIG. 4a

| Well | % positive 1 | 2 | 3 | 4 | 5 |
|---|---|---|---|---|---|
| F-5 | 3.2 | 3.7 | 0.1 | 2.0 | 4.0 |
| F-6 | 2.7 | 2.3 | 1.3 | 6.9 | 5.0 |
| F-7 | 2.0 | 5.4 | 1.1 | 18.6 | 12.4 |
| F-8 | 15.8 | 48.8 | 2.3 | 38.0 | 10.2 |
| F-9 | 78.3 | 96.9 | 4.2 | 21.6 | 26.4 |
| F-10 | 12.9 | 98.8 | 31.9 | 14.1 | 7.2 |
| F-11 | 99.4 | 99.9 | 80.0 | 88.9 | 96.5 | Too high |
| F-12 | 69.6 | 88.0 | 31.6 | 46.8 | 47.0 |
| G-1 | 99.9 | 99.8 | 90.5 | 89.2 | 80.9 | Too high |
| G-2 | 5.0 | 14.9 | 0.5 | 16.0 | 49.6 |
| G-3 | 2.2 | 21.3 | 0.6 | 3.1 | 17.4 |
| G-4 | 3.4 | 4.1 | 0.5 | 4.5 | 3.9 |
| G-5 | 1.4 | 8.4 | 1.4 | 1.9 | 2.1 |
| G-6 | 87.7 | 98.7 | 63.4 | 30.7 | 68.1 |

H14s9/WNT protocol | Shef3.2/FGF protocol

% positive

| Well | 1 | 2 | 3 | 4 | 5 |
|---|---|---|---|---|---|
| F-2 | 78.5 | 63.5 | 83.7 | 52.3 | 36.9 |
| F-3 | 73.0 | 98.0 | 97.9 | 8.2 | 6.7 |
| F-4 | 93.5 | 69.0 | 77.7 | 22.3 | 23.4 |

H14s9/WNT protocol (wells 1–3) | Shef3.2/FGF protocol (wells 4–5)

Line/protocol-specific result: F-3 wells 1–3; F-2 & F-4 wells 4–5 (highlighted)

FIG. 5

% positive

| Well | 1 | 2 | 3 | 4 | 5 | |
|---|---|---|---|---|---|---|
| B-9 | 74.8 | 82.4 | 53.6 | 66.5 | 2.8 | CD15 |
| C-8 | 99.8 | 95.8 | 97.4 | 4.3 | 21.6 | GD2 |
| C-11 | 95.7 | 85.3 | 89.7 | 34.8 | 29.1 | SSEA1 |
| C-12 | 71.3 | 53.5 | 75.0 | 80.1 | 11.0 | SSEA4 |

H14s9/WNT protocol (wells 1–3) | Shef3.2/FGF protocol (wells 4–5)

HUMAN OTIC PROGENITOR IDENTIFICATION AND ISOLATION

CROSS REFERENCE TO RELATED APPLICATIONS

The present application is a continuation of U.S. patent application Ser. No. 16/329,935, filed Mar. 1, 2019, which is a national phase application of International Application No. PCT/GB2017/052707 filed Sep. 14, 2017, which claims priority to and filing benefit of United Kingdom Patent Application No. 1615714.1 filed Sep. 15, 2016, each of which are incorporated herein by reference in their entireties.

The present invention relates generally to the identification and isolation of human otic progenitor cells. More specifically, the present invention relates to a method of using cell markers to identify and isolate human otic progenitor cells from a mixed population of cells, methods of enrichment and production of human otic progenitor cells, and associated kits for use in identification and/or isolation.

Deafness is a condition with a high prevalence worldwide, produced primarily by the loss of the sensory hair cells and their associated spiral ganglion neurons (SGNs). Of all the forms of deafness, auditory neuropathy is of particular concern. This condition, defined primarily by damage to the SGNs with relative preservation of the hair cells, is responsible for a substantial proportion of patients with hearing impairment. Although the loss of hair cells can be circumvented partially by a cochlear implant, no routine treatment is available for sensory neuron loss, as poor innervation limits the prospective performance of an implant. Using stem cells to recover the damaged sensory circuitry is a potential therapeutic strategy.

Protocols have been developed to induce differentiation from human embryonic stem cells (hESCs) using signals, such as FGF3 and FGF10, involved in the initial specification of the otic placode (Chen et al. 2012. *Restoration of auditory evoked responses by human ES-cell-derived otic progenitors*. Nature, 490(7419):278-82. doi: 10.1038/nature 11415). The induced otic progenitors are able to differentiate in vitro into hair-cell-like cells and auditory neurons that display expected electrophysiological properties. Moreover, when transplanted into an auditory neuropathy model, otic neuroprogenitors engraft, differentiate and significantly improve auditory-evoked response thresholds. However, the FGF3/10 induction method used is inefficient, yielding approximately 20% of the required cell types only.

If otic progenitors derived from human embryonic stem cells (hESCs) are to be used in a clinical setting, it is essential that those cells can be isolated from other cell types inadvertently produced during the differentiation process. An established method to separate out component cell populations from heterogeneous cultures is Fluorescence-Activated Cell Sorting (FACS), but to use this method, specific cell-surface markers must be identified that bind to the key cell-type e.g. otic progenitors. Although a variety of markers have been described to isolate generic neural progenitors, none has been identified to isolate human otic progenitors (either neural or epithelial).

An aim of the present invention is to provide a method of identifying, and potentially isolating human otic progenitors from mixed populations of cells.

INVENTION SUMMARY

According to a first aspect of the present invention, there is provided a method of identifying human otic progenitor cells in a mixed population of cells using at least two cell surface markers selected from SSEA1 (also known as CD15 or Lewis x), GD3, TRA-2-49 (alkaline phosphatase), SSEA4, GD2 and CD141.

According to another aspect of the present invention, there is provided a method of identifying human otic progenitor cells in a mixed population of cells comprising determining if a cell has at least two cell surface markers selected from SSEA1, GD3, TRA-2-49, SSEA4, GD2 and CD141.

According to another aspect of the present invention, there is provided a method of identifying human otic progenitor cells in a mixed population of cells comprising determining if a cell has at least two cell surface markers selected from SSEA1, GD3, TRA-2-49, SSEA4, GD2 and CD141,
  wherein cells identified as having:
   a) at least two of SSEA1, GD3, TRA-2-49, SSEA4, or GD2; or
   b) at least one of SSEA1, GD3, TRA-2-49, SSEA4, GD2, and not CD141,
   are identified as human otic progenitor cells.

According to another aspect of the present invention, there is provided a method of identifying human otic progenitor cells in a mixed population of cells using at least two cell surface markers selected from SSEA1 (also known as CD15), GD3, TRA-2-49 (alkaline phosphatase), SSEA4, GD2 and CD141, the method comprising:
  providing binding members specific for at least two different cell markers (i.e. the at least two different cell markers are selected from SSEA1 (also known as CD15), GD3, TRA-2-49 (alkaline phosphatase), SSEA4, GD2 and CD141);
  contacting the mixed population of cells with the binding members; and
  detecting the binding or non-binding of the binding members to cells in the mixed population of cells.

According to another aspect of the present invention, there is provided a method of enriching human otic progenitor cells from a mixed population of cells, the method comprising:
  identifying the human otic progenitor cells in accordance with the invention herein; and
  sorting the cells such that human otic progenitor cells are isolated from non-otic progenitor cells, such that the human otic progenitor cells are enriched in the population.

According to another aspect of the present invention, there is provided a method of producing a population of human otic progenitor cells, the method comprising:
  differentiating non-otic progenitor cells into human otic progenitor cells, whereby some non-otic progenitor cells may remain in the population to form a mixed population of cells; and
  enriching the human otic progenitor cells from the mixed population of cells in accordance with the method of the invention herein.

According to another aspect of the present invention, there is provided a kit comprising at least two different binding members, wherein the binding members are arranged to bind to different cell markers selected from SSEA1, GD3, TRA-2-49, SSEA4, GD2 and CD141.

According to another aspect of the present invention, there is provided the use of CD141 as a negative cell marker to identify non-otic progenitor cells in a mixed population of cells.

Advantageously, the cell markers SSEA1, GD3, TRA-2-49, SSEA4, GD2 and CD141 have been identified through multiple rounds of screenings using a panel of cell surface antibodies on two different human embryonic stem cell lines, differentiated into otic progenitors using two different methods. Using objective, quantitative thresholds of expression and qualitative, morphological analysis of otic progenitor morphology the following markers were selected that labelled the correct cell type. Moreover, CD141 was identified as a negative marker i.e. it labels cells that are not otic progenitors. The cell surface proteome of human pluripotent stem cell-derived otic progenitors have been characterized using antibodies that can be employed in flow cytometry and fluorescent automated cell sorting (FACS) in order to purify them from the heterogenous populations generated from differentiating pluripotent stem cells. The isolation and purification can a) improve the direct application for cell therapy, by better defining the appropriated cell type and removing potentially hazardous cells and b) improve the in vitro assays for drug screening and toxicity by removing cells that could have a confounding effect. Furthermore, these markers should be very useful to purify otic progenitors in order to: 1) Make them differentiate further into either sensory hair cells or neurons. This should make differentiation protocols more efficient, facilitating the scaling up of preparations for high throughput drug screenings; and 2) Select the appropriate cell type for cell transplantation therapy, minimizing the contamination with unwanted cell types and reducing the potential risks of the therapy of developing side effects.

BRIEF DESCRIPTION OF THE DRAWINGS

FIGS. 1A and 1B—Induction of hES cells towards an otic progenitor fate is achieved through induction of FGF signalling with FGF3 and FGF10 (FIG. 1A). Improved yield of progenitors has been achieved through the addition of WNT-inactivation for the first 9 days, followed by WNT-activation for 3 days with a simultaneous reduction in FGF3 and FGF10 concentration (FIG. 1B).

FIG. 4a—Wells highlighted will not be considered as potential hits, i.e below the threshold.

FIG. 4b—Wells highlighted will not be considered as potential hits, i.e. above the threshold.

FIG. 4c—The antibody corresponding to well F-3 only bound to cells of the H14 s9 line that had been treated with IWR-1 and BIO. As it is not common to both lines and protocols, it is not considered further as a candidate.

FIG. 5—Percentages of the selected markers detected in the BD Lyoplate screening. SSEA1 was represented twice (as the H198 antibody—labelled as CD15- and as the MC480 antibody—labelled as SSEA1). GD3 and TRA-2-49/6E were not represented in the BD Lyoplates and only selected from our initial small panel.

DETAILED DESCRIPTION

Figure 2A:
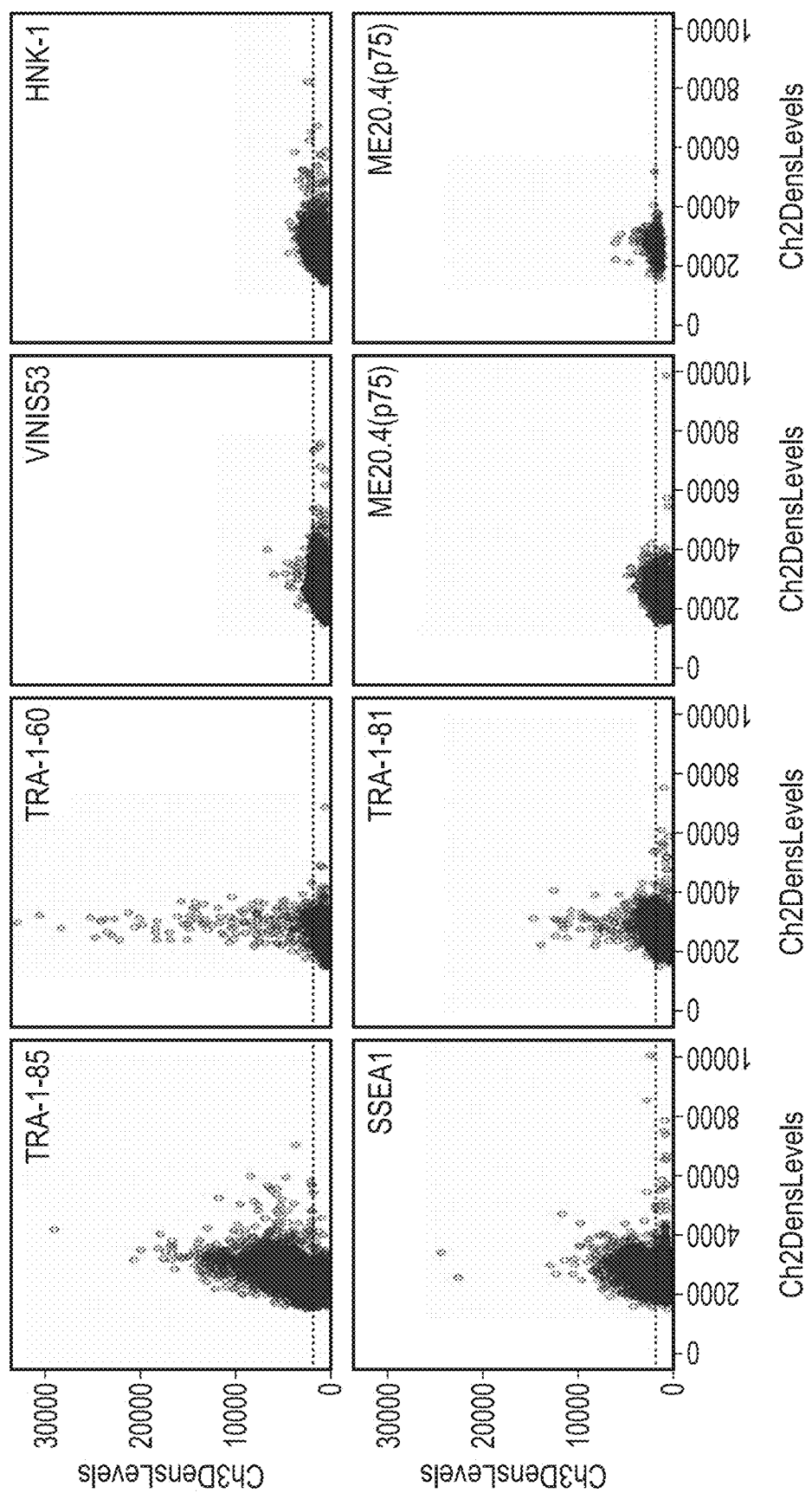
FIGS. 2A, 2B, and 2C—Dot plots generated from the fluorescence intensities of individual cells (plate 1 data), GFP levels from the endogenous reporter on the x-axis and Alexa 568 from the secondary targeting the cell surface marker antibodies on the y-axis (FIGS. 2A, 2B, and 2C).

According to a first aspect of the present invention, there is provided a method of identifying human otic progenitor cells in a mixed population of cells using at least two cell surface markers selected from SSEA1 (also known as CD15 or Lewis x), GD3, TRA-2-49 (alkaline phosphatase), SSEA4, GD2 and CD141.

According to another aspect of the present invention, there is provided a method of identifying human otic progenitor cells in a mixed population of cells comprising determining if a cell has at least two cell surface markers selected from SSEA1, GD3, TRA-2-49, SSEA4, GD2 and CD141.

According to another aspect of the present invention, there is provided a method of identifying human otic progenitor cells in a mixed population of cells comprising determining if a cell has at least two cell surface markers selected from SSEA1, GD3, TRA-2-49, SSEA4, GD2 and CD141,
   wherein cells identified as having:
   a) at least two of SSEA1, GD3, TRA-2-49, SSEA4, or GD2; or
   b) at least one of SSEA1, GD3, TRA-2-49, SSEA4, GD2, and not CD141,
   are identified as human otic progenitor cells.

In one embodiment, the cell markers SSEA1, GD3, TRA-2-49, SSEA4, and GD2 are positive cell markers and CD141 is a negative cell marker. Suitably, the methods involve measuring the positive cell markers. Suitably, the methods involve measuring the negative cell markers. The methods may also involve measuring positive and negative cell markers.

Using cell surface markers as described herein may comprise using them in an identification/determination step. In particular the determination if the cell surface marker is present or not present on a cell, or present or not present on a group of cells. The positive cell markers may be used in combination with each other to identify human otic progenitors, for example at least in pairs of positive markers (i.e. two or more of the positive markers). In another embodiment at least three of the positive cell markers are used in combination. In another embodiment at least four of the positive cell markers are used in combination. In another embodiment all five (i.e. five of the) positive cell markers of SSEA1, GD3, TRA-2-49, SSEA4, and GD2 are used to identify human otic progenitor cells in a mixed population of cells.

The positive cell markers may also be used in combination with the negative cell marker CD141. In one embodiment at least one (i.e. one of the) positive cell marker selected from SSEA1, GD3, TRA-2-49, SSEA4, and GD2 is used in combination with the CD141 negative cell marker. In another embodiment at least two (i.e. two of the) positive cell markers selected from SSEA1, GD3, TRA-2-49, SSEA4, and GD2 are used in combination with the CD141 negative cell marker. In another embodiment at least three (i.e. three of the) positive cell markers selected from SSEA1, GD3, TRA-2-49, SSEA4, and GD2 are used in combination with the CD141 negative cell marker. In another embodiment at least four (i.e. four of the) positive cell markers selected from SSEA1, GD3, TRA-2-49, SSEA4, and GD2 are used in combination with the CD141 negative cell marker. In another embodiment all five (i.e. five of the) positive cell markers of SSEA1, GD3, TRA-2-49, SSEA4, and GD2 are used in combination with the CD141 negative cell marker.

The method may comprise the use of at least two cell markers, the at least two cell markers comprising SSEA1 and GD3. The method may comprise the use of at least two positive cell markers, the at least two positive cell markers comprising SSEA1 and GD3, and the negative cell marker CD141. The method may comprise the use of at least two cell markers, the at least two cell markers comprising SSEA1 and TRA-2-49. The method may comprise the use of at least two positive cell markers, the at least two positive cell markers comprising SSEA1 and TRA-2-49, and the negative cell marker CD141. The method may comprise the use of at least two cell markers, the at least two cell markers comprising SSEA1 and SSEA4. The method may comprise the use of at least two positive cell markers, the at least two positive cell markers comprising SSEA1 and SSEA4, and the negative cell marker CD141. The method may comprise the use of at least two cell markers, the at least two cell markers comprising SSEA1 and GD2. The method may comprise the use of at least two positive cell markers, the at least two positive cell markers comprising SSEA1 and GD2, and the negative cell marker CD141. The method may comprise the use of at least two cell markers, the at least two cell markers comprising GD3 and TRA-2-49. The method may comprise the use of at least two positive cell markers, the at least two positive cell markers comprising GD3 and TRA-2-49, and the negative cell marker CD 141. The method may comprise the use of at least two cell markers, the at least two cell markers comprising GD3 and SSEA4. The method may comprise the use of at least two positive cell markers, the at least two positive cell markers comprising GD3 and SSEA4, and the negative cell marker CD141. The method may comprise the use of at least two cell markers, the at least two cell markers comprising GD3 and GD2. The method may comprise the use of at least two positive cell markers, the at least two positive cell markers comprising GD3 and GD2, and the negative cell marker CD141.

The method may comprise the use of at least two cell markers, the at least two cell markers comprising TRA-2-49 and SSEA4. The method may comprise the use of at least two positive cell markers, the at least two positive cell markers comprising TRA-2-49 and SSEA4, and the negative cell marker CD141. The method may comprise the use of at least two cell markers, the at least two cell markers comprising TRA-2-49 and GD2. The method may comprise the use of at least two positive cell markers, the at least two positive cell markers comprising TRA-2-49 and GD2, and the negative cell marker CD141. The method may comprise the use of at least two cell markers, the at least two cell markers comprising SSEA4 and GD2. The method may comprise the use of at least two positive cell markers, the at least two positive cell markers comprising SSEA4 and GD2, and the negative cell marker CD141.

The use of cell markers in combination may be simultaneously (at substantially the same time), or sequentially (at different times/steps) in the identification. In one embodiment, the use of cell markers in combination is simultaneous, for example in FACS and/or MACS.

The mixed population of cells may otherwise be referred to as a heterogeneous cell population. The mixed population of cells may be in vitro. The method of the invention may be in vitro. In one embodiment, the mixed population of cells may be provided from, or during, an in vitro stem cell (such as hESCs or any other pluripotent stem cells like iPSCs) differentiation protocol. In another embodiment, the mixed population of cells may be provided from, or during de-differentiating, trans-differentiating or direct reprogramming procedures into human otic cell lineages.

In another embodiment, the mixed population of cells may be provided from tissue, for example from a biopsy. Sources of human otic progenitor cells may be any tissue known to one of skill in the art, including but not limited to developing foetal inner ear tissues, and cochlear and vestibular samples obtained from surgical interventions from adult inner ears.

The mixed population of cells may be mammalian. In one embodiment, the cells of the mixed population of cells are human.

A further embodiment the method may be used for identification of human otic progenitor cells in vivo, for example post-operatively during or after a cell transplantation treatment.

The method of identification may comprise targeting the cell markers with a binding member that is capable of detection, for example the binding of the binding member to the cell marker may be detectable. The mixed population of cells may be contacted with one or more binding members capable of binding (alternatively arranged to bind) to the cell markers.

The binding member may preferentially bind a cell marker described herein or otherwise be specific for a cell marker described herein. The binding member may comprise an antibody, antibody fragment, or a mimetic thereof.

In one embodiment, the binding member to identify/bind to SSEA1 comprises antibody HI98 or 480-1-1. In another embodiment, the binding member to identify/bind to SSEA1 may comprise a binding member, such as an antibody, capable of competing for binding with antibody HI98 or 480-1-1. In another embodiment, the binding member to identify/bind to SSEA1 may comprise a binding member, such as an antibody, capable of binding the same epitope as antibody HI98 or 480-1-1. In another embodiment, the binding member to identify/bind to SSEA1 may comprise an antibody having the same VL and VH chain as antibody HI98 or 480-1-1. In another embodiment, the binding member to identify/bind to SSEA1 may comprise an antibody having the same CDRs as antibody HI98 or 480-1-1.

In one embodiment, the binding member to identify/bind to SSEA4 comprises antibody MC-813-70. In another embodiment, the binding member to identify/bind to SSEA4 may comprise a binding member, such as an antibody, capable of competing for binding with antibody MC-813-70. In another embodiment, the binding member to identify/bind to SSEA4 may comprise a binding member, such as an antibody, capable of binding the same epitope as antibody MC-813-70. In another embodiment, the binding member to identify/bind to SSEA4 may comprise an antibody having the same VL and VH chain as antibody MC-813-70. In another embodiment, the binding member to identify/bind to SSEA4 may comprise an antibody having the same CDRs as antibody MC-813-70.

In one embodiment, the binding member to identify/bind to TRA-2-49 comprises antibody TRA-2-49/6E. In another embodiment, the binding member to identify/bind to TRA-2-49 may comprise a binding member, such as an antibody, capable of competing for binding with antibody TRA-2-49/6E. In another embodiment, the binding member to identify/bind to TRA-2-49 may comprise a binding member, such as an antibody, capable of binding the same epitope as antibody TRA-2-49/6E. In another embodiment, the binding member to identify/bind to TRA-2-49 may comprise an antibody having the same VL and VH chain as antibody TRA-2-49/6E. In another embodiment, the binding member to identify/bind to TRA-2-49 may comprise an antibody having the same CDRs as antibody TRA-2-49/6E.

In one embodiment, the binding member to identify/bind to GD2 comprises any one of antibodies 14.18, DMab-20, 14G2a, VIN 2 or PB22. In another embodiment, the binding member to identify/bind to GD2 may comprise a binding member, such as an antibody, capable of competing for binding with any one of antibodies 14.18, DMab-20, 14G2a, VIN 2 or PB22. In another embodiment, the binding member to identify/bind to GD2 may comprise a binding member, such as an antibody, capable of binding the same epitope as any one of antibodies 14.18, DMab-20, 14G2a, VIN 2 or PB22. In another embodiment, the binding member to identify/bind to GD2 may comprise an antibody having the same VL and VH chain as any one of antibodies 14.18, DMab-20, 14G2a, VIN 2 or PB22. In another embodiment, the binding member to identify/bind to GD2 may comprise an antibody having the same CDRs as any one of antibodies 14.18, DMab-20, 14G2a, VIN 2 or PB22.

In one embodiment, the binding member to identify/bind to GD3 comprises antibody DMab-7 or VINIS56. In another embodiment, the binding member to identify/bind to GD3 may comprise a binding member, such as an antibody, capable of competing for binding with antibody DMab-7 or VINIS56. In another embodiment, the binding member to identify/bind to GD3 may comprise a binding member, such as an antibody, capable of binding the same epitope as antibody DMab-7 or VINIS56. In another embodiment, the binding member to identify/bind to GD3 may comprise an antibody having the same VL and VH chain as antibody DMab-7 or VINIS56. In another embodiment, the binding member to identify/bind to GD3 may comprise an antibody having the same CDRs as antibody DMab-7 or VINIS56.

In one embodiment, the binding member to identify/bind to CD141 comprises antibody 1A4. In another embodiment, the binding member to identify/bind to CD141 may comprise a binding member, such as an antibody, capable of competing for binding with antibody 1A4. In another embodiment, the binding member to identify/bind to CD141 may comprise a binding member, such as an antibody, capable of binding the same epitope as antibody 1A4. In another embodiment, the binding member to identify/bind to CD141 may comprise an antibody having the same VL and VH chain as antibody 1A4. In another embodiment, the binding member to identify/bind to CD141 may comprise an antibody having the same CDRs as antibody 1A4.

The cell markers and antibodies arranged to bind the cell markers may be further described and identified in the following publications, which are herein incorporated by reference.

SSEA4 (Kannagi R, Cochran N A, Ishigami F, Hakomori S-i, Andrews P W, Knowles B B, Solter D. Stage-specific embryonic antigens (SSEA-3 and -4) are epitopes of a unique globo-series ganglioside isolated from human teratocarcinoma cells. EMBO J. 1983; 2:2355-2361.)

GD2 (Andrews P W, Nudelman E, Hakomori S-i, Fenderson B A. Different patterns of glycolipid antigens are expressed following differentiation of TERA-2 human embryonal carcinoma cells induced by retinoic acid, hexamtehylene bisacetamide (HMBA) or bromodeoxyuridine (BUdR) Differentiation. 1990; 43:131-138) and (Durbas M, Horwacik I, Boratyn E, Kamycka E, Rokita H, GD2 ganglioside specific antibody treatment downregulates PI3K/Akt/mTOR signaling network in human neuroblastoma cell lines. Int J Oncol. 2015 September; 47(3):1143-59. doi: 10.3892/ijo.2015.3070.)

SSEA1 (Solter D, Knowles B B. Monoclonal antibody defining a stage specific mouse embryonic antigen (SSEA1) Proc. Natl. Acad. Sci. USA. 1978; 75:5565-5569.)

GD3 (Andrews P W, Nudelman E, Hakomori S-i, Fenderson B A. Different patterns of glycolipid antigens are expressed following differentiation of TERA-2 human embryonal carcinoma cells induced by retinoic acid, hexamtehylene bisacetamide (HMBA) or bromodeoxyuridine (BUdR) Differentiation. 1990; 43:131-138) and (Stuhlmiller GM1, Roberson K M, Seigler H F., Serological response of non-human primates to human melanoma disialoganglioside GD3. Cancer Immunol Immunother. 1989; 29(3):205-10)

TRA-2-49 (Andrews PW1, Casper J, Damjanov I, Duggan-Keen M, Giwereman A, Hata J, von Keitz A, Looijenga L H, Millán J L, Oosterhuis J W, Pera M, Sawada M, Schmoll H J, Skakkebaek N E, van Putten W, Stern P, Comparative analysis of cell surface antigens expressed by cell lines derived from human germ cell tumours. Int J Cancer. 1996 Jun. 11; 66(6):806-16.)

CD141 (Mutin M, Dignat-George F, Sampol J. Immunologic phenotype of cultured endothelial cells: quantitative analysis of cell surface molecules. Tissue Antigens. 1997 November; 50(5):449-58.)

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced.

Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to as a "mAb".

As antibodies can be modified in a number of ways, the term "antibody" should b e construed as covering any specific binding member or substance having a binding domain with the required specificity. Thus, this term covers antibody fragments, derivatives, functional equivalents, mimetics and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. An antibody mimetic may comprise an affibody.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment which consists of a VH domain; (v) isolated CDR regions; (vi) F(ab')2 fragments, a bivalent fragment comprising two linked Fab fragments; and (vii) single chain Fv molecules (scFv), wherein a VH domain and a VL domain are linked by a peptide linker which allows the two domains to associate to form an antigen binding site.

The method of the invention may comprise a detection step, wherein the cell markers are detected as present or not present on a cell or group of cells.

The skilled person will understand that there are a number of methods to detect the binding of binding members, such as antibodies, to a cell surface marker. Such method may comprise labelling the binding member with a detectable label/tag or using a secondary binding member, such as an antibody, that is labelled or tagged and is capable of specifically binding to the "primary" binding member bound to the cell marker.

In one embodiment, the binding member is labelled (or otherwise tagged) for identification. Once a labelled binding member is bound to the cell marker the cell may be termed a "labelled cell". A different label may be used to label each species of binding member arranged to bind a cell marker. The label may comprise any of a radiolabel, an enzymatic label, a magnetic label, affinity label (such as biotin or avidin), or a light-emission detectable label, such as fluorophore or chromophore; or combinations thereof. The label may be conjugated to the binding member, such as by covalent bonding.

The fluorophore may be in the form of fluorescent proteins, such as GFP (green), YFP (yellow) or RFP (red). Alternatively, the fluorophore may be a non-protein organic fluorophore. Fluorophores that may be provided as labels may comprise any of the group selected from Xanthene derivatives, such as fluorescein, rhodamine, Oregon green, eosin, and Texas red; Cyanine derivatives, such as cyanine, indocarbocyanine, oxacarbocyanine, thiacarbocyanine, and merocyanine; Squaraine derivatives and ring-substituted squaraines, including Seta, SeTau, and Square dyes; Naphthalene derivatives (dansyl and prodan derivatives); Coumarin derivatives; oxadiazole derivatives, such as pyridyloxazole, nitrobenzoxadiazole and benzoxadiazole; Anthracene derivatives, such as anthraquinones, including DRAQ5, DRAQ7 and CyTRAK Orange; Pyrene derivatives, such as cascade blue; Oxazine derivatives, such as Nile red, Nile blue, cresyl violet, and oxazine 170; Acridine derivatives, such as proflavin, acridine orange, acridine yellow; Arylmethine derivatives, such as auramine, crystal violet, malachite green; and Tetrapyrrole derivatives, such as porphin, phthalocyanine, and bilirubin.

A different fluorophore may be used to label each species of binding member arranged to bind a cell marker. Each fluorophore has a characteristic peak excitation and emission wavelength that may be detected. Quantum dots may be used in place of traditional fluorophores.

An alternative binding member to antibodies may be provided by aptamers, short nucleotide sequences that can recognize specific protein domains. Because aptamers are small and change conformation upon binding of their target, they can be engineered so that specific binding releases a quencher or generates a FRET pair that can be detected.

The detection of labelled cells may be by any suitable assay, which may comprise the use of any of the group comprising immunoassays, spectrometry, western blot, ELISA, immunoprecipitation, slot or dot blot assay, isoelectric focussing, SDS-PAGE and antibody microarray immunohistological staining, radio immuno assay (RIA), fluoroimmunoassay, an immunoassay using an avidin-biotin or streptoavidin-biotin system, etc or combinations thereof. These methods are well known to persons skilled in the art. Some methods of detection may require the destruction of the cells. In some embodiments, the detection method may be none destructive for the cell. For example, detection may comprise microscopy, such as confocal and/or fluorescence microscopy, to identify labelled cells. The detection may comprise the use of FACS (Fluorescence-activated cell sorting) or MACS (Magnetic-activated cell sorting). In one embodiment, detection comprises the use of FACS.

According to another aspect of the present invention, there is provided a method of identifying human otic progenitor cells in a mixed population of cells using at least two cell surface markers selected from SSEA1 (also known as CD15), GD3, TRA-2-49 (alkaline phosphatase), SSEA4, GD2 and CD141, the method comprising:
  providing binding members specific for at least two different cell markers (i.e. wherein the cell markers are selected from SSEA1 (also known as CD15), GD3, TRA-2-49 (alkaline phosphatase), SSEA4, GD2 and CD141);
  contacting the mixed population of cells with the binding members; and
  detecting the binding or non-binding of the binding members to cells in the mixed population of cells.

The method may further comprise the determination that a cell is an human otic progenitor cell if:
  a) binding members arranged to bind to the positive cell markers bind to at least two different positive cell markers on the cell; or
  b) a binding member arranged to bind one of the positive cell markers binds to at least one of the positive cell markers on the cell, and a binding marker arranged to bind to the negative cell marker CD141 does not bind to the cell.

In another embodiment, the method may further comprise the determination that a cell is an human otic progenitor cell if
  a) binding members arranged to bind to the positive cell markers bind to at least three different positive cell markers on the cell; or
  b) binding members arranged to bind at least two different positive cell markers bind to the at least two different positive cell markers on the cell, and a binding marker arranged to bin d to the negative cell marker CD141 does not bind to the cell.

According to another aspect of the present invention, there is provided a method of enriching human otic progenitor cells from a mixed population of cells, the method comprising:

identifying the human otic progenitor cells in accordance with the invention herein; and sorting the cells such that human otic progenitor cells are isolated from non-otic progenitor cells, such that the human otic progenitor cells are enriched in the population.

In one embodiment, the isolation of the human otic progenitor cells may be complete (i.e. 100% isolation from non-otic progenitor cells). In another embodiment, the human otic progenitor cells may be enriched such that there are less than 20% non-otic progenitor cells in the population. In another embodiment, the human otic progenitor cells may b e enriched such that there are less than 15% non-otic progenitor cells in the population. In another embodiment, the human otic progenitor cells may be enriched such that there are less than 10% non-otic progenitor cells in the population. In another embodiment, the human otic progenitor cells may be enriched such that there are less than 8% non-otic progenitor cells in the population. In another embodiment, the human otic progenitor cells may be enriched such that there are less than 5% non-otic progenitor cells in the population. In another embodiment, the human otic progenitor cells may be enriched such that there are less than 3% non-otic progenitor cells in the population. In another embodiment, the human otic progenitor cells may be enriched such that there are less than 2% non-otic progenitor cells in the population. In another embodiment, the human otic progenitor cells may be enriched such that there are less than 1% non-otic progenitor cells in the population. In another embodiment, the human otic progenitor cells may be enriched such that there are less than 0.1% non-otic progenitor cells in the population. In another embodiment, the human otic progenitor cells may be enriched such that there are less than 0.01% non-otic progenitor cells in the population.

The enrichment may be after a single round of sorting. Alternatively, multiple round s of sorting may be provided, for example to further enrich or ensure a higher percentage of human otic progenitors in the population.

The non-otic progenitor cells may be discarded, destroyed, sequestered, or otherwise contained separately from the human otic progenitor cells.

In one embodiment, the enrichment process maintains viability of the human otic progenitor cells.

In one embodiment, the sorting is by FACS. In another embodiment, the enriching and sorting of human otic progenitor cells is by the use of at least one affinity column. Alternatively, the method can be with the use of magnetic beads which selectively bind the human otic progenitor cells. In another embodiment, the enriching and sorting of human otic progenitor cells is by the use of MACS.

Advantageously, the use of FACS provides enrichment and cell sorting with high accuracy and reduces the need for multiple sorting passes, because FACS allows the use of multiple different fluorophore labels, and therefore multiple cell marker selection, at the same time.

According to another aspect of the present invention, there is provided a method of producing a population of human otic progenitor cells, the method comprising:

differentiating, de-differentiating, trans-differentiating or directed reprogramming a population of non-otic progenitor cells into human otic progenitor cells, whereby some non-otic progenitor cells may remain in the population to form a mixed population of cells; and enriching the human otic progenitor cells from the mixed population of cells in accordance with the method of the invention herein.

Differentiating a population of non-otic progenitor cells may comprise differentiating a population of stem cells, such as hESCs or iPSCs. For example, the non-otic progenitor cells may comprise stem cells, such as hESCs or iPSCs. De-differentiating a population of non-otic progenitor cells may comprise de-differentiating a population of more mature cells. For example, the non-otic progenitor cells may comprise mature (fully differentiated) cells. Trans-differentiation or directed reprogramming a population of non-otic progenitor cells may comprise Trans-differentiation or directed reprogramming a population of cells from a different lineage (i.e. non-otic lineage).

Many differentiation agents are known to one of skill in the art which can differentiate stem cells into specific types of cells, such as otic progenitor cells. Therefore, it is envisioned that the stem cells may be differentiated into otic progenitor cells by any means known to one of skill in the art. Some examples of differentiation agents, include, but are not limited to FGF ligands, WNT inhibition and activation, IGF1, TGF inhibition and activation, fetal calf serum, nerve growth factor, removal of EGF, removal of bFGF (or both), BDNF, thyroid hormone, BMPs, LIF, sonic hedgehog, GDNFs, VEGFs, interleukins, interferons, SCF, activins, inhibins, chemokines, retinoic acid and CNTF.

The differentiation may be in accordance with, but not limited to, the protocol described by Chen et al. (2012. Restoration of auditory evoked responses by human ES-cell-derived otic progenitors. *Nature*, 490(7419):278-82. doi: 10.1038/naturel 1415), or Ronaghi et al. (2014. *Stem Cells Dev*, 23(11), 1275-1284), which are herein incorporated by reference. For example, the differentiation may comprise inducing otic progenitor cells from human embryonic stem cells (hESCs) using signals involved in the initial specification of the otic placode. In particular, differentiation may comprise FGF (fibroblast growth factor) induction with FGF3 and FGF10, optionally wherein the FGF3 and FGF10 concentration are each about 50 ng/ml. The differentiation may comprise the steps described in FIG. 1a herein or Chen et al. 2012. Alternatively, differentiation may comprise FGF induction with FGF3 and FGF10, and manipulation of WNT signalling by WNT-inhibition followed by WNT induction (see FIG. 1b herein). The differentiation may comprise the steps described in FIG. 1b herein.

It is envisioned that the non-otic progenitor cells may be stem cells from any known source, embryonic (fetal) tissue or post-embryonic tissue. In one embodiment the non-otic progenitor cells for differentiation comprise or consist of pluripotent stems cells, such as human embryonic stem cells (hESCs) or induced pluripotent stem cells (iPSCs). The non-otic progenitor cells may comprise foetal cells. In another embodiment, the non-otic progenitor cells may comprise stem cells from other tissues, such as mesenchymal tissue, fat tissue, or other tissues.

According to another aspect of the present invention, there is provided a kit comprising at least two different binding members, wherein the binding members are arranged to bind to different cell markers selected from SSEA1, GD3, TRA-2-49, SSEA4, GD2 and CD141.

In one embodiment, the kit may comprise at least three different binding members, wherein the binding members are arranged to bind to different cell markers selected from SSEA1, GD3, TRA-2-49, SSEA4, GD2 and CD141.

In another embodiment, the kit may comprise at least four different binding members, wherein the binding members are arranged to bind to different cell markers selected from SSEA1, GD3, TRA-2-49, SSEA4, GD2 and CD141.

In another embodiment, the kit may comprise at least five different binding members, wherein the binding members are arranged to bind to different cell markers selected from SSEA1, GD3, TRA-2-49, SSEA4, GD2 and CD141.

In another embodiment, the kit may comprise a panel of binding members, wherein the panel of binding members comprises a binding member specific for each of the cell markers of SSEA1, GD3, TRA-2-49, SSEA4, GD2 and CD141.

The binding members of the kit may comprise antibodies as described herein. The binding members of the kit may be labeled as described herein.

In one embodiment, the binding member of the kit for use to identify/bind to SSEA1 comprises antibody HI98 or 480-1-1. In another embodiment, the binding member of the kit for use to identify/bind to SSEA1 may comprise a binding member, such as an antibody, capable of competing for binding with antibody HI98 or 480-1-1. In another embodiment, the binding member of the kit for use to identify/bind to SSEA1 may comprise a binding member, such as an antibody, capable of binding the same epitope as antibody HI98 or 480-1-1. In another embodiment, the binding member of the kit for use to identify/bind to SSEA1 may comprise an antibody having the same VL and VH chain as antibody HI98 or 480-1-1. In another embodiment, the binding member of the kit for use to identify/bind to SSEA1 may comprise an antibody having the same CDRs as antibody HI98 or 480-1-1.

In one embodiment, the binding member of the kit for use to identify/bind to SSEA4 comprises antibody MC-813-70. In another embodiment, the binding member of the kit for use to identify/bind to SSEA4 may comprise a binding member, such as an antibody, capable of competing for binding with antibody MC-813-70. In another embodiment, the binding member of the kit for use to identify/bind to SSEA4 may comprise a binding member, such as an antibody, capable of binding the same epitope as antibody MC-813-70. In another embodiment, the binding member of the kit for use to identify/bind to SSEA4 may comprise an antibody having the same VL and VH chain as antibody MC-813-70. In another embodiment, the binding member of the kit for use to identify/bind to SSEA4 may comprise an antibody having the same CDRs as antibody MC-813-70.

In one embodiment, the binding member of the kit for use to identify/bind to TRA-2-49 comprises antibody TRA-2-49/6E. In another embodiment, the binding member of the kit f or use to identify/bind to TRA-2-49 may comprise a binding member, such as an antibody, capable of competing for binding with antibody TRA-2-49/6E. In another embodiment, the binding member of the kit for use to identify/bind to TRA-2-49 may comprise a binding member, such as an antibody, capable of binding the same epitope as antibody TRA-2-49/6E. In another embodiment, the binding member of the kit for use to identify/bind to TRA-2-49 may comprise an antibody having the same VL and VH chain as antibody TRA-2-49/6E. In another embodiment, the binding member of the kit for use to identify/bind to TRA-2-49 may comprise an antibody having the same CDRs as antibody TRA-2-49/6E.

In one embodiment, the binding member of the kit for use to identify/bind to GD2 comprises any one of antibodies 14.18, DMab-20, 14G2a, VIN 2 or PB22. In another embodiment, the binding member of the kit for use to identify/bind to GD2 may comprise a binding member, such as an antibody, capable of competing for binding with any one of antibodies 14.18, DMab-20, 14G2a, VIN 2 or PB22. In another embodiment, the binding member of the kit for use to identify/bind to GD2 may comprise a binding member, such as an antibody, capable of binding the same epitope as any one of antibodies 14.18, DMab-20, 14G2a, VIN 2 or PB22. In another embodiment, the binding member of the kit for use to identify/bind to GD2 may comprise an antibody having the same VL and VH chain as any one of antibodies 14.18, DMab-20, 14G2a, VIN 2 or PB22. In another embodiment, the binding member of the kit for use to identify/bind to GD2 may comprise an antibody having the same CDRs as any one of antibodies 14.18, DMab-20, 14G2a, VIN 2 or PB22.

In one embodiment, the binding member of the kit for use to identify/bind to GD3 comprises antibody DMab-7 or VINIS56. In another embodiment, the binding member of the kit for use to identify/bind to GD3 may comprise a binding member, such as an antibody, capable of competing for binding with antibody DMab-7 or VINIS56. In another embodiment, the binding member of the kit for use to identify/bind to GD3 may comprise a binding member, such as an antibody, capable of binding the same epitope as antibody DMab-7 or VINIS56. In another embodiment, the binding member of the kit for use to identify/bind to GD3 may comprise an antibody having the same VL and VH chain as antibody DMab-7 or VINIS56. In another embodiment, the binding member of the kit for use to identify/bind to GD3 may comprise an antibody having the same CDRs as antibody DMab-7 or VINIS56.

In one embodiment, the binding member of the kit for use to identify/bind to CD 141 comprises antibody 1A4. In another embodiment, the binding member of the kit for use to identify/bind to CD141 may comprise a binding member, such as an antibody, capable of competing for binding with antibody 1A4. In another embodiment, the binding member of the kit for use to identify/bind to CD141 may comprise a binding member, such as an antibody, capable of binding the same epitope as antibody 1A4. In another embodiment, the binding member of the kit for use to identify/bind to CD141 may comprise an antibody having the same VL and VH chain as antibody 1A4. In another embodiment, the binding member of the kit for use to identify/bind to CD141 may comprise an antibody having the same CDRs as antibody 1A4.

The kit may further comprise reagents or binding members suitable for detection of the label.

According to another aspect of the present invention, there is provided the use of CD141 as a negative cell marker to identify non-otic progenitor cells in a mixed population of cells.

The use may comprise the determination of the presence or absence of CD 141 on a cell.

A further embodiment is the use of the human otic progenitor cell surface markers, both positive and negative, to study stem and human otic progenitor cell behavior during development and in maturity.

A further embodiment of the invention is the use of the human otic progenitor cell-specific cell markers as targets for pharmacological manipulation of human otic progenitor cells, in vivo, and in vitro following isolation or differentiation.

An "otic progenitor cell" as used herein is a cell which is a biological cell that, like a stem cell, has a tendency to differentiate into specific types of cells, but is already more specific than a stem cell and is pushed to differentiate into an auditory related cell, such as hair-cell-like cells or auditory neurons. A difference between stem cells and progenitor cells is that stem cells can replicate indefinitely, whereas progenitor cells can divide only a limited number of times. Current methods of identification can include a series of transcription factors used as molecular markers, such as PAX2, PAX8, FOXG1, SOX2 to name a few. Otic progenitor cells are found in vivo, during foetal development, in the otic placode, the otocyst and in the prosensory region of the prospective sensory epithelia. Their presence in the adult, mature ear is still under debate. Some supporting cells, however, may have progenitor-like properties. As used herein the application describes aspects related to human otic progenitors. However, all aspects described herein in relation to human otic progenitors may also be understood to refer to mammals more generally.

The term "positive cell surface marker" used herein is understood to mean a marker, such as a molecule, that is on the surface of otic progenitors and can be used, perhaps with other markers, to positively verify the identity of the otic progenitors. Reference to "positive cell surface marker" or "positive cell marker" herein is intended to refer to one of SSEA1, GD3, TRA-2-49, SSEA4, or GD2.

The term "negative cell surface marker" used herein is understood to mean a marker, such as a molecule, that is on the surface of a cell, which is not found on otic progenitors. Therefore, cells having such a negative marker can be verified as non-otic progenitor. Reference to "negative cell surface marker" or "negative cell marker" herein is intended to refer to CD141.

The term "enrich" or "enriched" used herein is intended to mean that the proportion of otic progenitor cells is increased in a population of cells relative to non-otic progenitor cells. The enrichment may otherwise be considered as sorting otic progenitor cells from non-otic progenitor cells. In enrichment, otic progenitor cells may be isolated from non-otic progenitor cells or vice versa.

The invention does not preclude the use of the cell markers described herein in combination with other known or future identified cell markers.

"Specific" or "specific binding" is generally used to refer to the situation in which one member of a specific binding pair will not show any significant binding to molecules other than its specific binding partner(s), and, e.g., has less than about 30% cross reactivity with any other molecule. In other embodiments it has less than 20%, 10%, or 10% cross reactivity with any other molecule. In this context, a binding member that is "arranged to bind" to a particular cell marker is a binding member that is capable of specifically binding to the cell marker i.e. it is configured to bind to said marker without significant binding of other molecules. Where the context allows, the terms "arranged to bind" and "specifically bind" can be used interchangeably.

The skilled person will understand that optional features of one embodiment or aspect of the invention may be applicable, where appropriate, to other embodiments or aspects of the invention.

Having now generally described the invention, the following examples are offered to illustrate, but not to limit the claimed invention.

Examples

The work leading to this invention has received funding from the European Union Seventh Framework Programme FP7/HEALTH-2013-INNOVATION-1 under Grant Agreement Number 603029.

Purification of Otic Progenitors from Heterogeneous Cell Populations

Introduction

The Need for Prospective Purification of Otic Progenitors

Protocols optimised to direct hPSCs yield (at best) populations of cells with high representation of the desired cell type due to a number of key limitations in our ability to control stem cells. Problems such as heterogeneous starting cultures, batch-to-batch variation in growth factors, medium and other consumables, cell line variability and cell seeding density can all affect the efficiency of differentiation. A number of protocols have been developed for generating otic progenitors from hPSCs [1,2], but all give rise to mixed cultures with only a subset being the progenitors themselves. Currently, otic differentiation experiments are manually cleaned to purify for progenitors, which involves scraping off the unwanted cell types based on morphology and/or the expression of reporter genes. Whilst this approach has been effective facilitating down-stream neuronal/hair cell differentiations, it is both labour-intensive and prone to carry-over a small proportion of non-progenitor cell types. Hence, for stem cell therapies to progress towards clinical applications, a more precise objective method that can be scaled up to large cell numbers is required.

Fluorescence-activated cell sorting (FACS) is a commonly used technique to separate sub-groups of cells within a population based on the differential expression of cell surface markers. The method requires identification of unique cell surface protein expression profiles in the cells that are to be sorted out of a heterogeneous population, combined with the availability of suitable antibodies for those proteins. We have been screening antibodies known to attach to cell surface antigens in cultures of hESCs that have undergone otic differentiation to identify candidates for use in FACS to purify otic progenitors.

Protocols have been developed to drive hPSCs along otic differentiation lineages towards sensory neuron and hair cell phenotypes via intermediate states referred to as 'otic progenitors'. The protocols used to derive otic progenitors involve FGF induction with FGF3 and FGF10 (FIG. 1a and Chen et al 2012), and a more recent method that incorporates the manipulation of WNT signalling, adding a WNT-inhibition stage (using IWR-1-endo) followed by WNT induction (with BIO) (FIG. 1b).

Antibody screening has been undertaken on heterogeneous cell populations resulting from the above two protocols in an effort to find suitable cell surface markers that can be used to purify the otic progenitor populations via FACS.

Methods and Results hESCs from Shef3.2, H14-NOP-SOX2 reporter and H14s9 cultures were differentiated in 96 well plates using either the 'FGF protocol' (FIG. 1a) or the 'WNT protocol' (FIG. 1b). The resulting cultures were live stained with panels of cell surface antibodies before fixation and imaging in the IN Cell Analyser 2200. There were three stages of screening:

1. Pilot screen using CSCB antibodies. H14-NOP-SOX2 reporter line and WNT protocol used.
2. Main screen using BD lyoplate human cell surface marker screening panel with 242 antibodies. H14s9 line and WNT protocol used. (3 replicate plates)
3. Main screen using BD lyoplate human cell surface marker screening panel with 242 antibodies. Shef3.2 line and FGF protocol used. (2 replicate plates)

After imaging, data was processed using the Developer Toolbox software and further analysed with Excel and SPSS. The three experiments are summarised in table 1.

TABLE 1

'PILOT' was done using CSCB antibody panel, 'BD RUN' done using the BD Lyoplate Human Cell Surface Marker screening panel.

|  | PILOT | BD RUN 1 | BD RUN 2 |
|---|---|---|---|
| LINE | H14-NOP-SOX2 | H14s9 | Shef3.2 |
| REPLICATE PLATES | 2 | 3 | 2 |

1.1 Pilot screening using the CSCB-Sheffield Antibody Panel

The initial phase of the screening utilised a relatively small panel of antibodies available at the Centre for Stem Cell Biology in Sheffield (Table 2).

TABLE 2

Panel of Centre for Stem Cell Biology antibodies used for initial screening CSCB antibody panel P3X AG (−ve control)
TRA-1-85 (+ve control)
480-1-1 (aka SSEA1, CD15)
813-70 (aka SSEA4)
TRA-1-60s
TRA-1-81
TRA-2-49/6E
ME20.4 (aka P75)
B159
TRA-2-10
VINIS 53
ME311
HNK-1
VIN2 PB22 (aka GD2)
VINIS 56 (aka GD3)
A2B5

A hESC reporter line that expresses EGFP driven by a nasal-and-otic placode-specific SOX2 enhancer was differentiated using the 'WNT' protocol (FIG. 1b). Live staining was carried out using the antibody panel at the end of otic induction (~12 days), and cells were then fixed before all were probed with Hoechst and imaged using an automated microscopy system (IN Cell Analyser 2200, GE Healthcare). Using the Developer software, individual cells were identified based on Hoechst expression, then the fluorescence intensity of both GFP (SOX2 reporter within the cells) and Alexa 568 (the fluorochrome attached to the secondary antibody used against the cell surface marker antibodies) was recorded and used to define positive expression in each cell. Positivity was defined as a fluorescence intensity higher than seen in unreactive IgG, negative control wells (IgGs produced by the parental myeloma P3X63Ag8 line).

Two 96 well plates were used in this primary screen varying only slightly in the staining method: plate 1 stained according to the BD Lyoplate bioimaging protocol using 5% FBS in DMEM as growth medium with antibodies added to and plate 2 as per plate 1 but with 5% FBS in PBS (with $CaCl_2$ and $MgCl_2$) in place of growth medium.

Figure 2B:
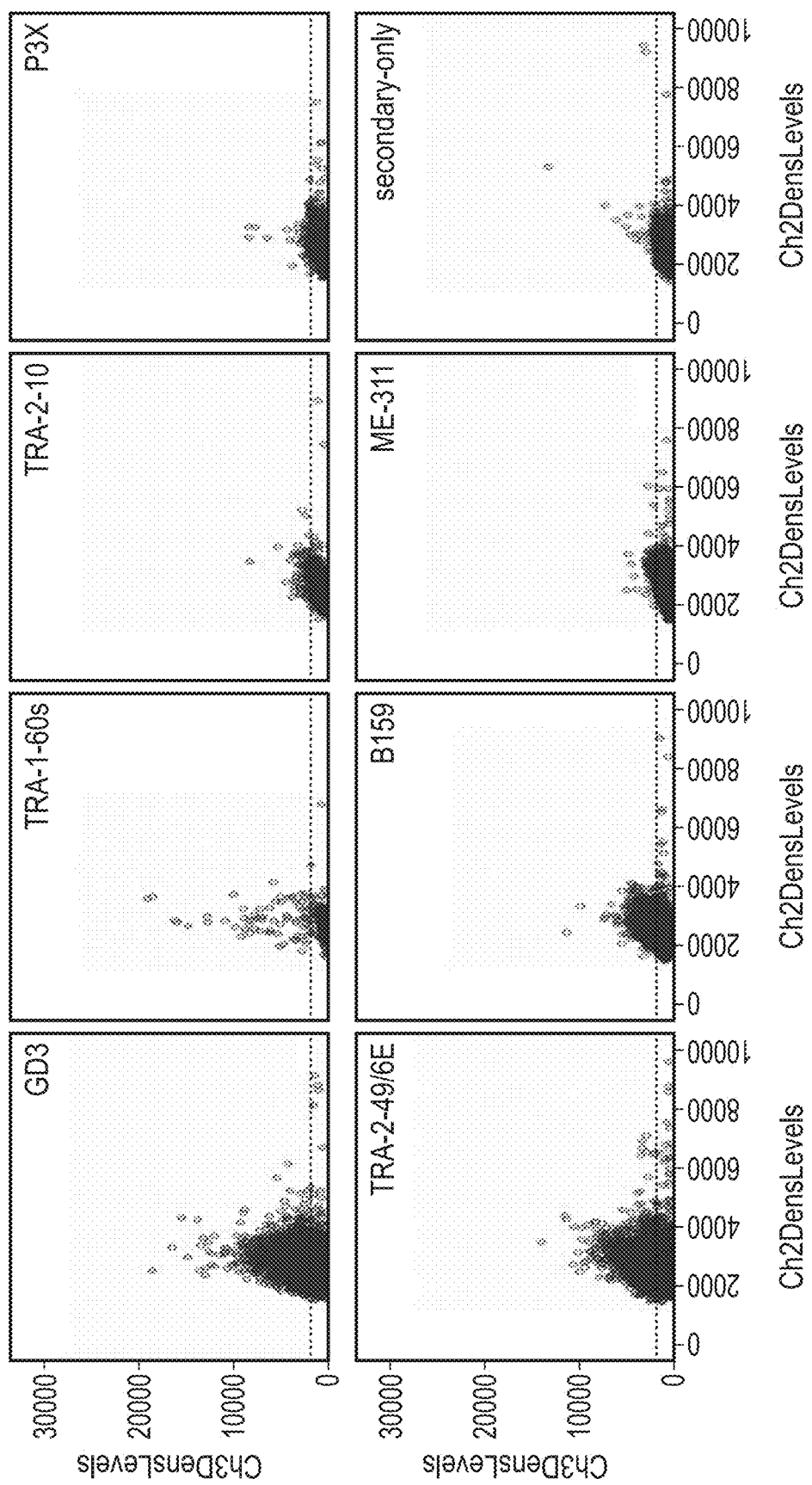
Figure 2C:
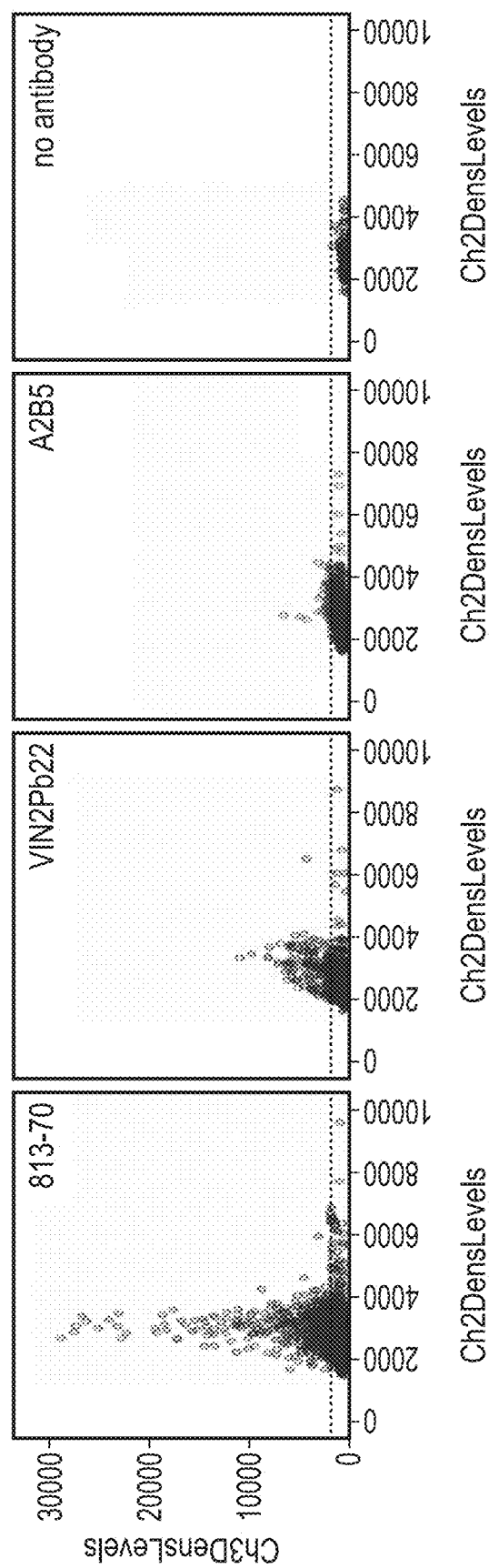

A number of potential hits were revealed in the CSCB antibody panel. FIGS. 2A, 2B, and 2C show the data from this experiment displayed with each antibody in a separate pane, x-axis referring to fluorescence intensity of the SOX2 reporter (GFP) and y-axis referring to fluorescence intensity of the cell surface marker. The panes are arranged from top to bottom based on the proportion of cells positive for the cell surface marker with top left being the most positive and bottom right being the least positive. TRA-1-85 is a positive control antibody, P3X is a negative control antibody. The top hits are found in the first column through to the poorest candidates in the last.

A different method of analysis based on the percentage of cells positive in each well, and the number of replicate wells per antibody that scored positive at either >25% or >10% thresholds confirmed the top three hits as SSEA1, GD3 and TRA-2-49, with SSEA4 (813-70) immediately below.

There was little difference between the antibody incubations done in PBS or in DMEM, so DMEM was chosen for future experiments as it forms a component of the differentiation medium the cells are grown in during otic induction. Live staining was not found to adversely affect the cells in any obvious way (i.e. no extra detachment of cells during the protocol), and is recommended in the BD Lyoplate methods as prior fixation can give rise to false results. Live staining would also be more appropriated for future applications when live progenitors are needed for further manipulations.

1.2 Initial Verification of Hits from the CSCB Panel

Figure 3:
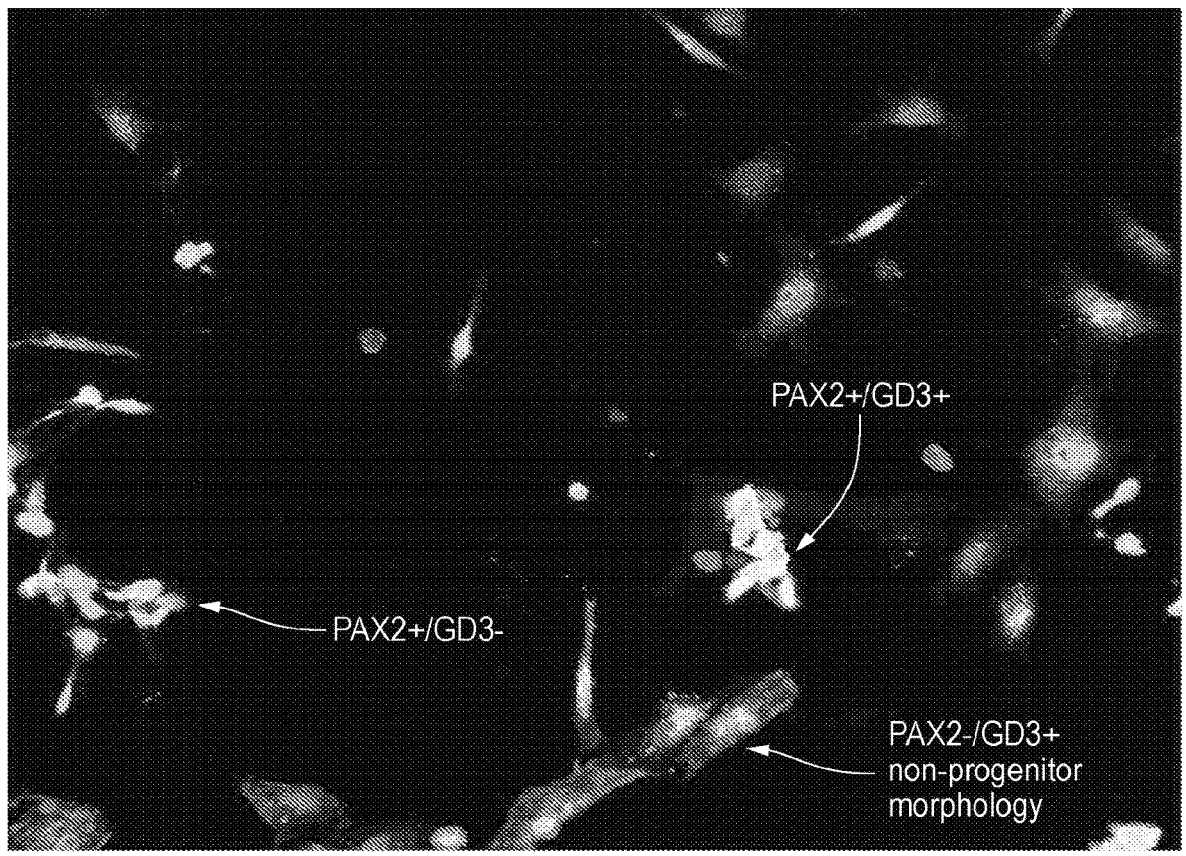
FIG. 3—GD3 (red), PAX2 (green) and Hoechst (blue) images merged. Arrows indicate: PAX2+/GD3− colony of otic neuronal progenitor morphology, PAX2+/GD3+ colony of otic epithelial progenitors and PAX2−/GD3+ cells not predicted to be otic progenitors based on morphology.

The SSEA-1 and GD3 antibodies were chosen for verification that they effectively bind to the otic progenitor subpopulation. To liberate the GFP channel on the microscope, we returned to the parental hESC line from which the reporter was generated, H14s9. The cells were differentiated in the same way as in the primary screen then live-stained with SSEA-1 and GD3 antibodies (in multiple, separate wells i.e. not looking at co-expression of the surface protein s). The cells were then fixed and permeabilised so that they could be probed for the nuclear (transcription) otic markers, PAX2, SOX2 and FOXG1. Hoechst was again used to identify the nuclei of individual cells. The same data collection and analysis methods were used as in the primary screen. These data indicate that the SSEA1 positive population is a subset of the cells positive for each of the three transcription factors (Table 3i). Data for GD3 is similar, except that a proportion (3.4%) of cells that are GD3 positive are not PAX2 positive (Table 3ii). This combined with morphological data showing GD3 staining of some cells not associated with an otic progenitor morphology suggests that GD3 is less discriminating of the desired cell subset than SSEA1. See FIG. 3.

TABLE 3i

Percentage of cells positive for otic progenitor markers and SSEA1.

| Antibodies | +/+ | +/− | −/+ | −/− |
|---|---|---|---|---|
| PAX2/SSEA1 | 7.2 | 40.0 | 0.5 | 52.3 |
| FOXG1/SSEA1 | 5.9 | 78.2 | 0.1 | 15.7 |
| SOX2/SSEA1 | 7.3 | 79.4 | 0.2 | 13.2 |

TABLE 3ii

Percentage of cells positive for otic progenitor markers and GD3.

| Antibodies | +/+ | +/− | −/+ | −/− |
|---|---|---|---|---|
| PAX2/GD3 | 7.2 | 45.3 | 3.4 | 44.0 |
| FOXG1/GD3 | 8.6 | 75.7 | 0.2 | 15.4 |
| SOX2/GD3 | 8.6 | 78.5 | 0.4 | 12.4 |

2.1 Screening of the BD Lyoplate Antibody Panel

Work with the CSCB Antibody Panel both proved the feasibility of using the automated bioimaging method to screen for cell surface markers and enabled thorough optimisation of the system prior to undertaking a more comprehensive screen based on the BD Lyoplate Human Cell Surface Marker Screening Panel (BD Biosciences). This panel assays the binding of 242 antibodies and was expected to extend the number of markers identified.

The BD lyoplate screen allows 5 replicates to be run in 96 well plates. We divided the experiment in two. Three replicates were done using the H14s9 cell line differentiated using the WNT protocol, while the remaining two used the Shef3.2 cell line with the FGF protocol. This experimental design had therefore included 5 total replicates, covering 2 independent cell lines and 2 different differentiation protocols. We believed that this would maximize the chances of pulling out the very best candidates for otic progenitor surface markers.

After processing the data, analysis was undertaken to identify the total number of cells in the well and those that are taken to be positive. The positive threshold was calculated on a plate-by-plate basis through analysis of well A1 which is defined as a control (primary antibody free) on each plate. The percentage of positive cells was then calculated for every well. This data was then collated for each of the 3 BD antibody plates i.e. 5 replicates for each plate, 3 for H14s9 and 2 for SHef3.2.

Two different type of analysis were then employed, first using intensity-based, objective criteria and later using morphology-based, subjective criteria.

Objective Analysis of Labelling Thresholds

1. We gave each well a percentage-positive value and list all 5 replicates side-by-side for comparison.
2. Cells that were <10% positive were classified negative, ≥10% were classified positive.
3. IF 3 or more replicate wells were negative then the well and corresponding antibody were classified non-candidates and removed from future consideration.
4. IF all 4 or 5 wells are >80% positive, antibody is considered not to be discriminatory enough (i.e. binding too many cell types) and hence classified non-candidates and removed from future consideration.
5. We checked the remaining wells had a minimum of 3 positive replicates which sp an the two cell lines i.e. if replicates 1-3 are positive (the H14s9 replicates) but 4 and 5 are both negative (the Shef3.2 replicates) then the well should be excluded as this suggests the antibody is binding specifically to one line (or possibly only to cells that have undergone differentiation via the WNT protocol as opposed to the FGF protocol).

FIG. 4 shows cut-outs of part of the plate 1 data used to illustrate how the criteria explained above were implemented. Data for wells F5 to G6 are displayed and the percentage data has been formatted such that the higher the percentage, the darker the shading, to make it easier to see differences. Replicates 1-3 are the H14s9/WNT protocol replicates. Replicates 4 and 5 are the Shef3.2/FGF protocol replicates.

In FIG. 4a, the wells outlined fall into the 3 or more negative replicates (point 3 above) and are hence removed as non-candidates. In FIG. 4b, the wells outlined fall into the insufficiently discriminatory (point4 above) category and hence are removed as non-candidates. In FIG. 4c, the wells outlined fall into the line/protocol-specific binding category (point 5 above) so are also removed as non-candidates.

Subjective Analysis Based on Morphology

Once all the non-candidate wells had been removed, we returned to the image data and checked the remaining wells to see if the antibody was in fact binding to the population we would classify as otic progenitors by morphology alone. This analysis was only done on the Shef3.2 replicates, since the H14s9 were too confluent to gauge morphologies by eye.

Altogether, these analyses confirm three of the best candidates identified in the initial pilot screening (SSEA1, SSEA4 and GD2). GD3 and TRA2-49 (alkalinephosphatase) were not represented in the BD Lyoplate. Although there were some 'second tier' positive markers identified, they did not pass the stringent criteria setup in this initial study and only these five (SSEA1, SSEA4, GD2, GD3 and TRA2-49) are followed through.

Furthermore, we identified CD141 as an exclusion marker since it labels most other cell types but not the progenitors.

Figure 6:
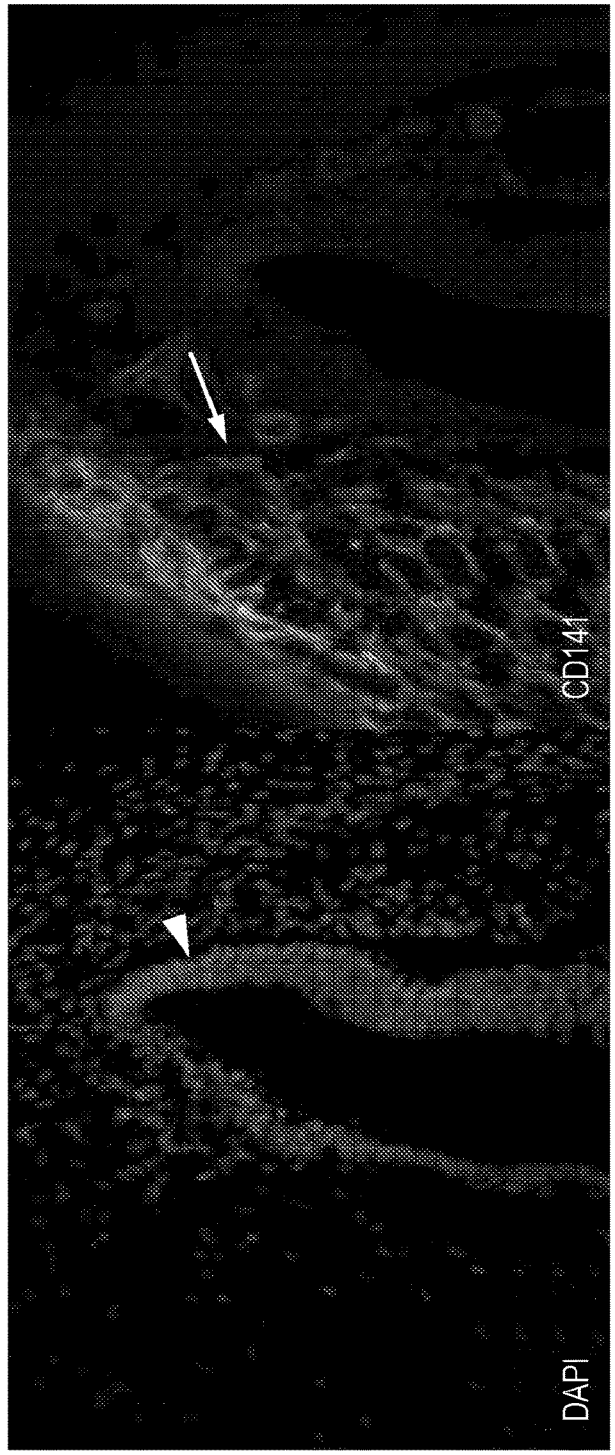
FIG. 6—Section of a 13 weeks-old human cochlear duct, stained for CD141. CD141 positive cells (arrow) are located outside the epithelia that contains otic progenitors (arrowhead).
Figure 7:
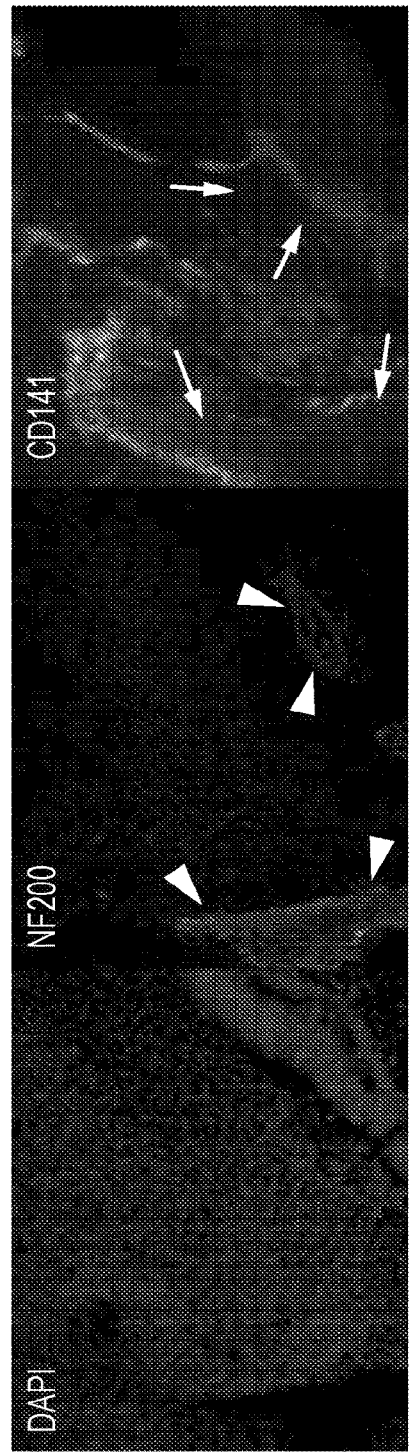
FIG. 7—Section of an 8 weeks-old cochlear duct, showing staining for CD141 and neurofilament (NF200). CD141 labels cells surrounding the cochlear epithelia, but excludes the NF200 positive neuroblasts (arrowheads in NF200-stained section, arrows in CD141-stained section).

Methods for FIGS. 6 and 7

Human fetuses of different gestational age were fixed for two hours in 4% PFA in PBS at 4° C. Samples were then cryoprotected in an ascending series of 5%-30% sucrose in PB S and embedded in Cryo-M-Bed (Bright), before being frozen in liquid iso-pentane cooled on liquid nitrogen. Ten μm thick serial sections were cut on a cryostat and collected onto gelatine-coated slides. Sections were briefly washed with PBS and incubated 15-30 minutes in blocking buffer (0.1% Triton 5% Normal Donkey Serum in PBS) at room temperature. Antibodies used were: anti-CD141 (Biolegend) and anti-neurofilament 200 (Sigma). Signals were visualized using Alexa-conjugated secondary antibodies. Nuclear counterstaining was done with DAPI (Sigma).

Figure 8A:
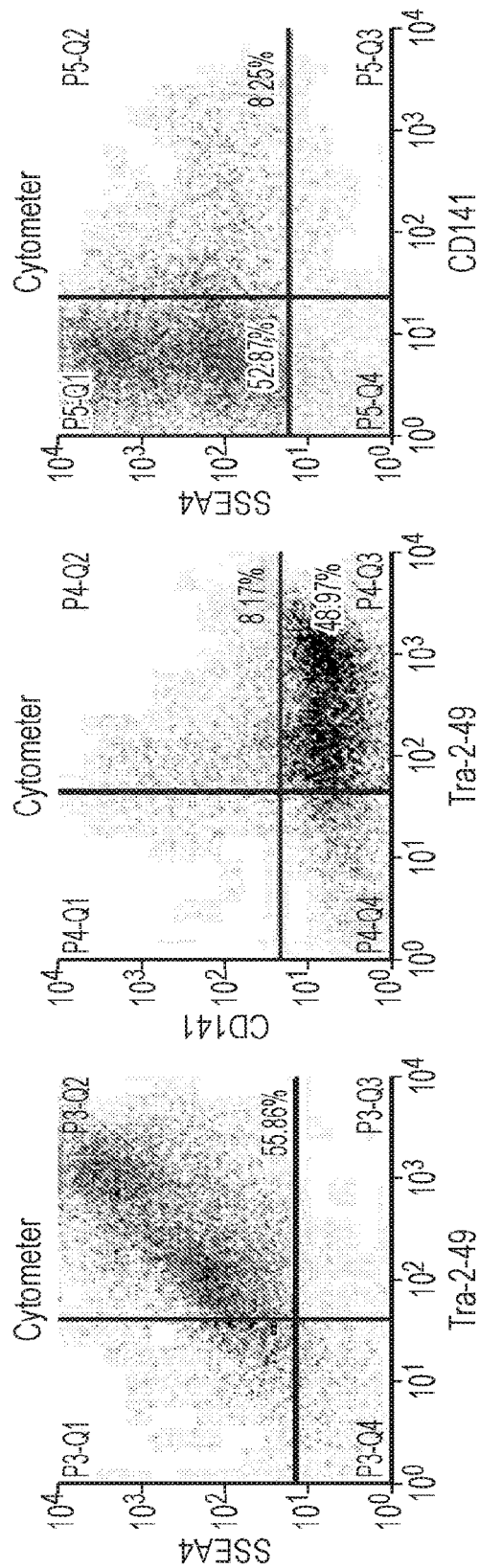
FIGS. 8a and 8b—hESCs differentiated into otic progenitors and stained for SSEA4, Tra-2-49 and CD141. (A) and (B) show two independent experiments. SSEA4 and TRA-2-49 colocalise to the same cell population (left column) ((A) P3-Q2 55.86%; (B) P3-Q2 65.15%), while most SSEA4/TRA-2-49 positive cells are CD141 negative ((A) P4-Q3 48.97%, P5-Q1 52.87%; (B) P4-Q3 65.82%, P5-Q1 66.79%). (A) and (B) display the more extreme examples, with CD141 positive cells ranging from ~0.3 to ~8% ((A) P4-Q2 8.17%, P5-Q2 8.25%; (B) P4-Q2 0.39%, P5-Q2 0.49%).
Figure 8B:
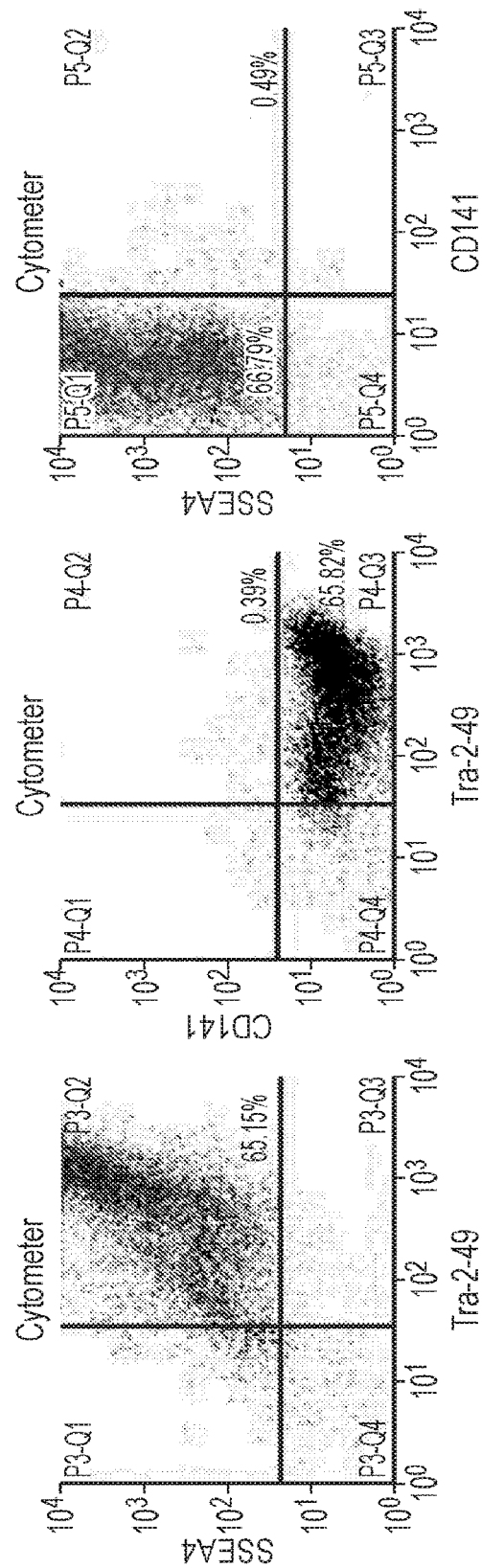
Figure 9:
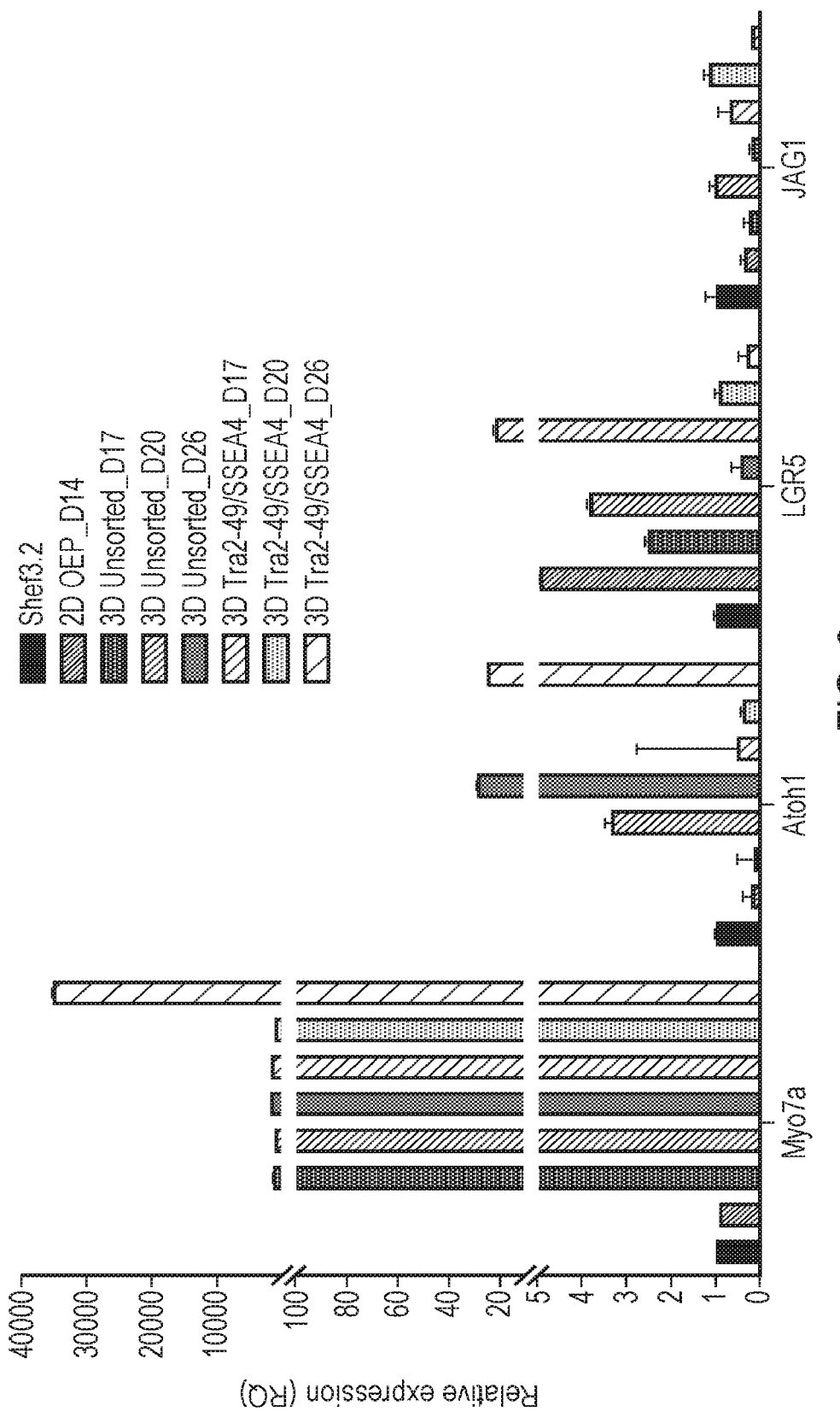
FIG. 9—hESCs were differentiated into otic progenitors for 14 days, and sorted for SSEA4/TRA2-49. Double positive cells were then allowed to differentiate for 17, 20 and 26 days into hair cell-like cells, using an organoide (3D) culture system developed in our lab. Differentiation into hair cell-like cells could also be accomplished using a published method (e.g Koehler et al, 2017). Unsorted cells were also differentiated alongside for comparison, and samples analysed by qPCR. Hair cell markers Myo7a and Atoh1 were upregulated in the sorted population, after 26 days of 3D culture. LGR5, a stem cell and supporting cell marker was upregulated in the immature progenitors before sorting, and during the early stages of differentiation mainly in the unsorted cell samples. JAG1, a supporting cell marker, was not upregulated.

Methods for FIGS. 8 and 9 hESCs from the Shef3.2 line were induced to differentiate into otic progenitors for 14 days using the 'FGF protocol', as described in [1]. At this stage, unfixed cells were labelled with SSEA4, TRA-2-49 and CD141 antibodies, directly conjugated to Alexa 647, Alexa 488 or Brilliant Violet 421 fluorochromes respectively (Biolegend). Cells were separated and analysed using a BD FACSJazz.

For FIG. 9, sorted and unsorted cells were allowed to differentiate further for 17, 20 and 26 days into hair cell-like cells, using an organoid (3D) culture system developed in our lab. Differentiation into hair cell-like cells could also be accomplished using a published method (e.g [2]). RNA was extracted and gene expression analysed by qPCR using a DD-Ct method.

These results suggest that the SSEA4+/TRA2-49+ double positive population contains progenitor cells capable of differentiating into the hair cell lineage, even when isolated from the non-SSEA4/TRA2-49 double positive fraction (single positive or −/− cells). The unsorted population was still able to differentiate, given that contains a relatively large percentage of SSEA4+/TRA2-49+ cells (54.8±5.6%, mean±s.e.m.).

REFERENCES

[1] Chen, W., Jongkamonwiwat, N., Abbas, L., Eshtan, S. J., Johnson, S. L., Kuhn, S., Milo, M., Thurlow, J. K., Andrews, P. W., Marcotti, W., Moore, H. D., Rivolta, M. N. "*Restoration of auditory evoked responses by human ES-cell-derived otic progenitors.*" Nature, 490, 278-282, 2012.

[2] Ronaghi, M., Nasr, M., Ealy, M., Durruthy-Durruthy, R., Waldhaus, J., Diaz, G. H., Joubert, L. M., Oshima, K., Heller, S. "*Inner ear hair cell-like cells from human embryonic stem cells.*" Stem Cells Dev, 23(11), 1275-1284, 2014.

The invention claimed is:

1. A method of identifying human otic progenitor cells in a mixed population of cells comprising determining if a cell has at least three cell surface markers selected from SSEA1, GD3, TRA-2-49, SSEA4, GD2, and CD141, wherein the cell markers SSEA1, GD3, TRA-2-49, SSEA4, and GD2 are positive cell markers, wherein the cell marker CD141 is a negative cell marker, wherein at least two positive cell markers are used in combination with the negative cell marker CD141, and wherein the mixed population of cells is provided from a population of pluripotent stem cells.

2. The method of claim 1, wherein the human otic progenitor cells are human otic neural progenitor cells.

3. The method of claim 1, wherein at least three, four, or five positive cell markers are used in combination to identify human otic progenitor cells.

4. The method of claim 1, wherein the pluripotent stem cells are human embryonic stem cells (hESCs).

5. The method of claim 1, wherein the pluripotent stem cells are induced-pluripotent stem cells (iPSCs).

6. The method of claim 1, wherein the mixed population of cells is contacted with one or more binding members arranged to bind to each cell marker.

7. The method of claim 6, wherein the binding member comprises an antibody, antibody fragment, or a mimetic thereof.

8. The method of claim 6, wherein the binding member is labeled for identification.

9. The method of claim 8, wherein the label comprises a fluorophore.

10. The method of claim 1, comprising a detection step, wherein the cell markers are detected as present or not present on a cell or group of cells.

11. The method of claim 10, wherein the detection step comprises the use of FACS and/or the use of MACS.

12. The method of claim 1, wherein the method comprises:
providing binding members specific for at least three different cell markers;
contacting the mixed population of cells with the binding members; and
detecting the binding or non-binding of the binding members to cells in the mixed population of cells.

13. The method of claim 12, wherein the method further comprises determining that a cell is a human otic progenitor cell if
binding members specific for at least two different positive cell markers bind to the at least two different positive cell markers on the cell, and a binding marker specific for the negative cell marker CD141 does not bind to the cell.

14. A method of enriching human otic progenitor cells from a mixed population of cells, the method comprising:
identifying human otic progenitor cells in accordance with the method of claim 1; and
sorting the cells such that the human otic progenitor cells are isolated from non-otic progenitor cells, such that the human otic progenitor cells are enriched in the population.

15. The method of claim 14, wherein the sorting comprises FACS and/or comprises MACS.

16. The method of claim 14, wherein the pluripotent stem cells are human embryonic stem cells (hESCs).

17. The method of claim 14, wherein the pluripotent stem cells are induced-pluripotent stem cells (iPSCs).

* * * * *